(12) United States Patent
Cabral

(10) Patent No.: US 7,179,588 B1
(45) Date of Patent: Feb. 20, 2007

(54) ASSAY FOR THE DETECTION OF PACLITAXEL RESISTANT CELLS IN HUMAN TUMORS

(75) Inventor: Fernando Cabral, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/574,099

(22) Filed: May 18, 2000

Related U.S. Application Data

(60) Provisional application No. 60/135,047, filed on May 20, 1999.

(51) Int. Cl.
*C12Q 1/68* (2006.01)
*G01N 33/53* (2006.01)

(52) U.S. Cl. .................. 435/6; 436/501; 436/518
(58) Field of Classification Search .............. 435/6, 435/4, 7.21, 7.23; 436/501, 504; 514/449
See application file for complete search history.

(56) References Cited

FOREIGN PATENT DOCUMENTS

WO   WO 00/71752   11/2000

OTHER PUBLICATIONS

Drexler et al (Leukemia and Lymphoma, 1993, 9:1-25).*
Embleton et al (Immunol Ser, 1984, 23:181-207).*

Hsu (in Tissue Culture Methods and Applications, Kruse and Patterson, Eds, 1973, Academic Press, NY, see abstract, p. 764).*
Gonzalez-Garay, Manuel L., A B-Tubulin Leucine Cluster Involved in Microtubule Assembly and Paclitaxel Resistance. Journal of Biological Chemistry vol. 274 (34) Aug. 20, 1999. pp. 23875-23882.
Nogales, Eva, et al. Structure of the xB Tubulin dimer by electron crystallography. Nature, vol. 391, Jan. 8, 1998, pp. 199-203. (XP-002143079).
Jordan, Allan, et al Tubulin as a Target for Antiancer Drugs: Agents Which Interact with the Mitotic Spindle. 1998 pp. 259-296. (XP-000886283).
Ginnakakou, Paraskevi, et. al. Paclitaxel-resistant Human Ovarian Cancer Cells have Mutant B-Tublins that Exhibit Impaired Paclitaxel-driven Polymerization. Journal of Biological Chemistry. vol. 272 (27) Jul. 4, 1997, pp. 17118-17125. (XP-002111288).
Cabral, Fernando, et al Resistance to Antimitotic Agents as Genetic Probes of Microtubule Structure and Function. Pharmac. Ther. vol. 52, pp. 159-171, 1991. (XP-000961706).

* cited by examiner

*Primary Examiner*—Misook Yu
(74) *Attorney, Agent, or Firm*—Williams, Morgan & Amerson, P.C.

(57) ABSTRACT

Tubulin mutations commonly associated with resistance to paclitaxel are defined, and PCR allele-specific primers capable of detecting the mutations in DNA from tumor cells are described as well as method for treating paclitaxel-resistant cells in tumors. A simple, rapid, and cost effective means for detecting paclitaxel-resistant cells in tumor biopsies from patients receiving paclitaxel therapy is disclosed.

28 Claims, 11 Drawing Sheets

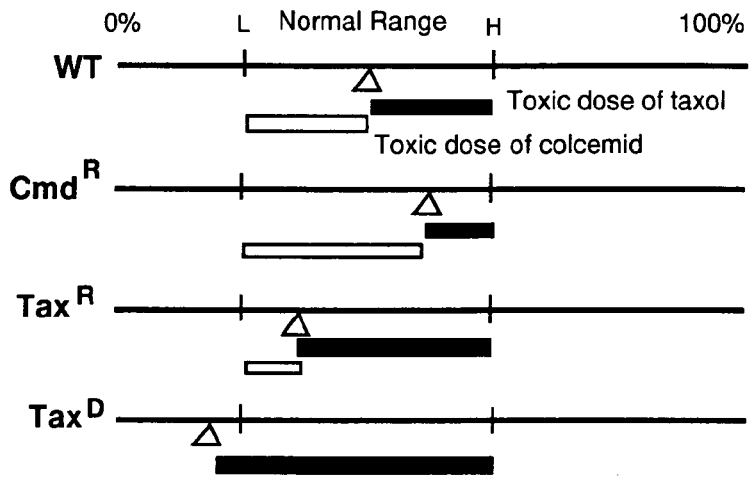

Figure 1: A mechanism to explain drug resistance in mutant CHO cells. The horizontal lines represent increasing stability and/or assembly (0 to 100%) of microtubules. We postulate that cells can survive only within a narrow range of stability (the "normal range") and that wild type cells, on average, have microtubule stability near the center of this range. The bars represent the level of drug (the toxic doses) required to shift stability outside the normal range. Thus, a toxic dose of taxol (solid bar) is the amount of drug that increases microtubule stability above "H," the high end of the normal range; while a toxic dose of colcemid (open bar) is the amount of drug needed to lower microtubule stability below "L," the low end of the normal range. Note that in colcemid resistant cells, the mutation has increased microtubule stability so that the cells can tolerate higher concentrations of colcemid but the cells are more sensitive to taxol. Conversely, in taxol resistant cells, the mutation has destabilized microtubules such that cells tolerate higher concentrations of taxol, but are sensitive to lower concentrations of colcemid. In taxol dependent (Tax$^D$) cells, the mutation shifts microtubule stability below the normal range so that the cells cannot divide unless taxol (or some other microtubule stabilizing agent) is added. This model is supported by direct measurements of microtubule assembly in mutant cell lines, and the mechanism of resistance has now gained wide acceptance (e.g. see Goodman & Gilman's "The Pharmacological Basis of Therapeutics," 9th ed., p. 1261; and Pratt & Ruddon's "The Anticancer Drugs," 2nd ed., p. 192).

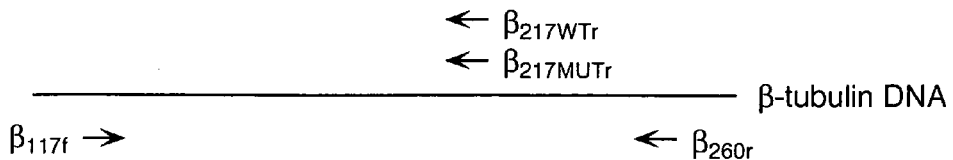

β₂₁₇WTr: CTCCGTAGGTGGGCGTGGTGA

β₂₁₇MUTr: CTCCGTAGGTGGGCGTGG_C_GC

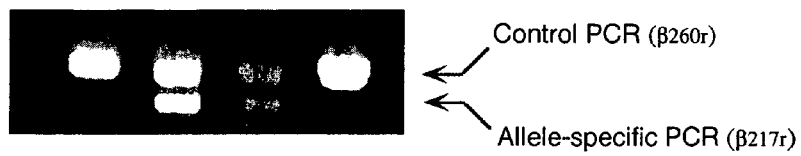

Figure 2: Allele-specific amplification of β-tubulin DNA. PCR reactions were carried out on WT and mutant DNA that differ by a single mutation that changes leu217 (CTC) to arg (CGC). Each reaction contained a forward primer (β117f), a common reverse primer (β260r), and a WT (β217WTr) or mutant (β217MUTr) allele-specific primer as indicated in the figure. (A): A diagram showing the relative positions of each primer on the DNA template. (B): The results of the PCR amplification. Upper band represents the control (β117f-β260r) amplification; lower band represents the allele specific (β117f-β217r) amplification. Note that the β217WTr primer amplifies WT but not mutant DNA, whereas the β217MUTr primer amplifies the mutant but not WT DNA. The β217WTr primer has a single 3' terminal mismatch (A:G) with the mutant DNA that is sufficient to prevent amplification. The β217MUTr primer has a 3' terminal mismatch (C:T) with WT DNA that is insufficient to prevent amplification. Therefore a second mismatch (C:A) was introduced at the third nucleotide from the 3' end (underlined in the sequence) to form the allele-specific primer. Note that a reduced amount of template was used for the PCR reaction in the third lane to demonstrate the necessity of including an in-tube control to normalize for problems during amplification.

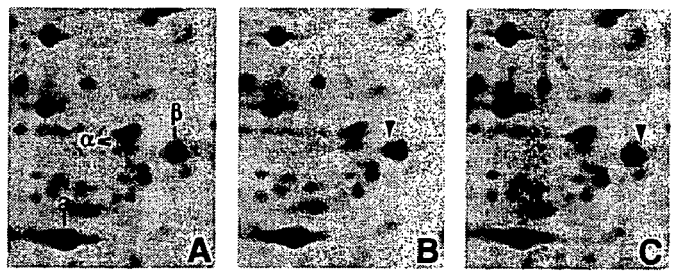

Fig. 3. Two-dimensional gels of paclitaxel resistant CHO cell lines. Cells were labeled with $^{35}$S-methionine, lysed in a Triton X-100 containing buffer, and analyzed by two-dimensional gel electrophoresis. The tubulin containing region of the autoradiograms is shown. Isoelectric focusing is from left (basic) to right (acidic); electrophoresis is from top (higher molecular weight) to bottom (lower molecular weight). A, Tax-18. Wild-type CHO cells exhibit an identical pattern. B, Tax 2-4. This and several other mutants have an additional β-tubulin spot (arrowhead) that migrates with a more basic isoelectric point. C, Tax 11-3. This mutant is unique in exhibiting an additional β-tubulin spot (arrowhead) that migrates with a more acidic isoelectric point. The positions of α-tubulin (α), β-tubulin (β), and actin (a) are indicated in panel A.

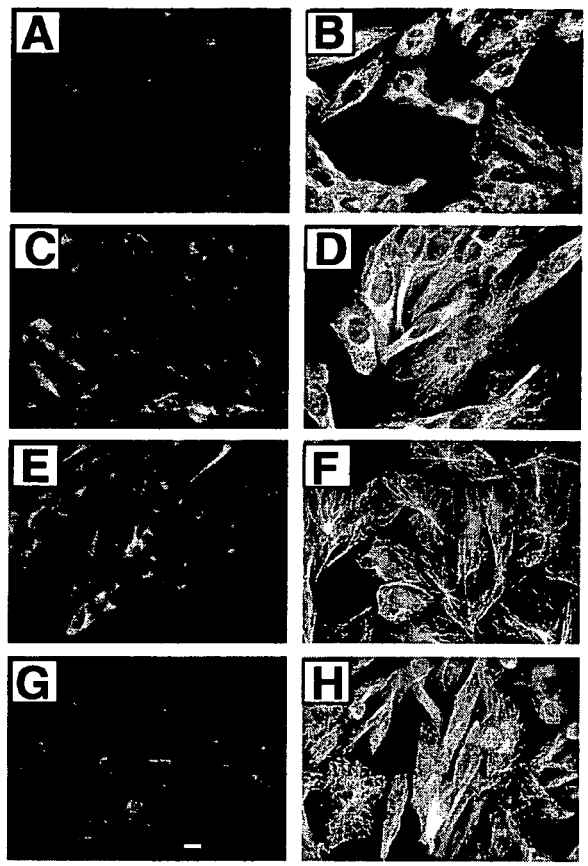

Fig. 4. Immunofluorescence of CHO cells stably transfected with mutant HAβ1-tubulin cDNAs. Cells from strain tTApuro 6.6 were transfected with HAβ1 (A, B), HAβ1$_{L215H}$ (C, D), HAβ1$_{L217R}$ (E, F), or HAβ1$_{L228F}$ (G, H) cDNA. G418-resistant colonies were then selected and screened for production of the HA-tagged tubulin using immunofluorescence with an antibody specific for the HA tag. Examples of some of the positive clones are shown. The cells were either maintained in tetracycline throughout their growth to repress expression of the transfected tubulin (A, C, E, G), or they were incubated for 24 h in medium without tetracycline to induce expression before analysis (B, D, F, H). Bar = 10 μm.

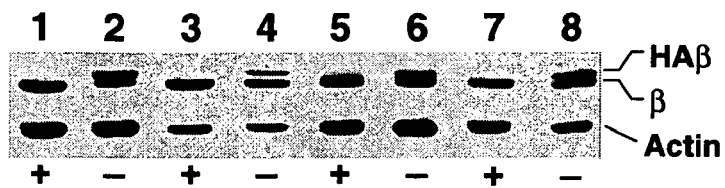

Fig. 5. Production of wild-type and mutant HAβ1-tubulin in transfected cell lines. Stably transfected cell lines were maintained in tetracycline to repress expression ("+" lanes) or were incubated 24 h in medium without tetracycline to induce expression ("-" lanes) and cellular proteins were then resolved by SDS gel electrophoresis, transferred onto nitrocellulose, and probed with antibodies specific for β-tubulin and actin. Shown in the figure are cells transfected with HAβ1 (lanes 1 and 2), HAβ1$_{L215H}$ (lanes 3 and 4), HAβ1$_{L217R}$ (lanes 5 and 6), and HAβ1$_{L228F}$ (lanes 7 and 8). Note that the HA tag causes HAβ1-tubulin (HAβ) to migrate more slowly than edogenous β-tubulin (β). An antibody to actin was included to indicate relative protein loading.

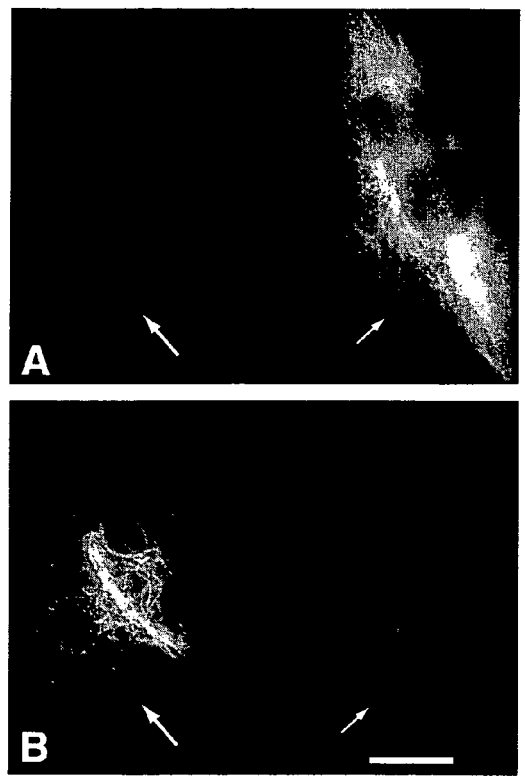

Fig. 6. Cells expressing HAβ1$_{L215H}$ have reduced α-tubulin acetylation. A G418 selected population of cells transfected with HAβ1$_{L215H}$ cDNA was grown 24 h without tetracycline and stained for immunofluorescence with antibodies to the HA tag (A) and to acetylated α-tubulin (B). Small arrows indicate a cell that expressed the mutant HAβ1-tubulin. Large arrows indicate a neighboring cell that failed to express the mutant HAβ1-tubulin. Note that acetylation was greatly reduced in the cell that expressed the mutant HAβ1-tubulin. Bar = 10 μm.

Fig. 7. Mutant HAβ1-tubulins confer paclitaxel resistance. Approximately 100 cells were seeded into replicate wells of 24-well dishes containing the indicated concentrations of paclitaxel (in ng/ml) with ("+") or without ("-") 1 mg/ml tetracycline. The cells were allowed to grow for 6-7 d and were then stained with methylene blue. The cell lines came from transfections with HAβ1 (A), HAβ1$_{L215H}$ (B), HAβ1$_{L217R}$ (C), or HAβ1$_{L228F}$ (D). Note that all cell lines had a similar sensitivity to the drug when cultured in the presence of tetracycline (no HAβ1-tubulin expression), but only the cells transfected with mutant forms of HAβ1-tubulin exhibited increased resistance to paclitaxel when cultured in the absence of tetracycline.

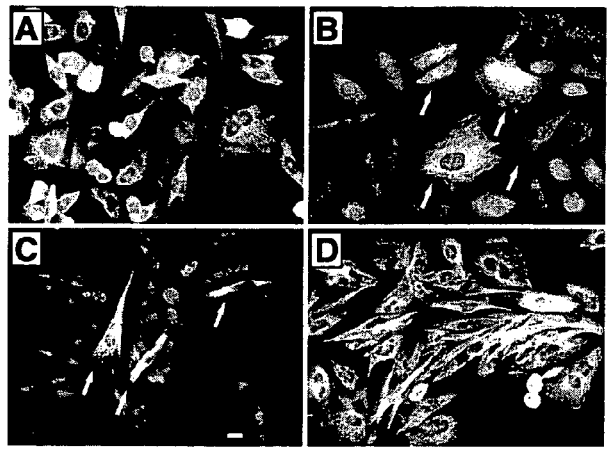

Fig. 8. Paclitaxel selects for transfected cells that express mutant HAβ1-tubulin. Cells transfected with HAβ1$_{L215H}$ cDNA were selected for resistance to G418 (A, B) or paclitaxel (C, D) either in the presence (A, C) or absence (B, D) of 1 mg/ml tetracycline. The total resistant cell population was then trypsinized and replated for 24 h in medium without tetracycline or paclitaxel before processing for immunofluorescence with an antibody specific for the HA tag. Arrows in B and C indicate cells that were positive for HAβ1$_{L215H}$-tubulin expression. Approximately 50% of the cells in panel A, and 100% of the cells in panel D were positive for expression. Note that G418 selects for cells that have taken up transfected DNA. These cells are only 50% positive for expression of mutant β-tubulin (panel A) because the tubulin gene may have been disrupted during integration into the DNA of some of the cells, or it may have integrated into a transcriptionally inactive area of the DNA. Even fewer positive cells are seen in G418 selected cells without tetracycline because high mutant β-tubulin expression is toxic. Cells selected in paclitaxel with tetracycline (C) gave only a few resistant cells. This population contains nonexpressing cells that gained spontaneous resistance to paclitaxel and sporadic positive cells in which expression of mutant β-tubulin is not regulated by tetracycline. Cells selected in taxol without tetracycline (D) are all positive showing that taxol is better than G418 at selecting for transfected cells that express the mutant tubulin. This is good evidence that expression of the mutant β-tubulin confers resistance to the drug. Bar = 10 μm.

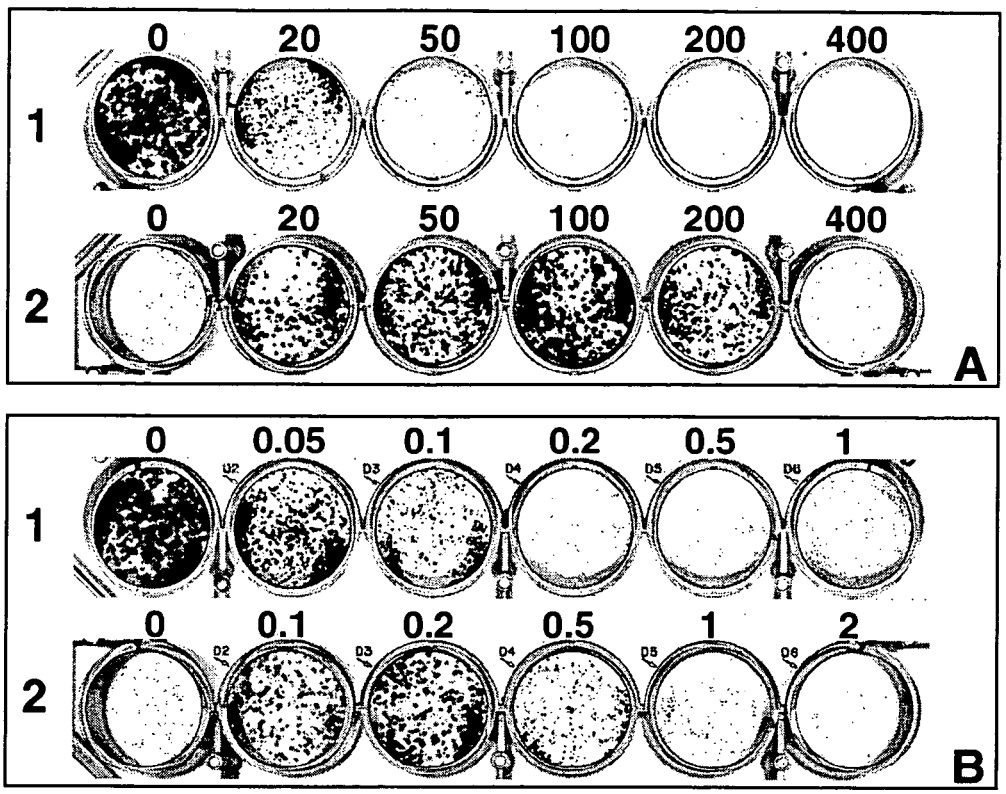

Fig. 9. Paclitaxel resistant cells are cross resistant to epothilone-B. Cells from wild-type (1) or paclitaxel dependent cell line Tax-18 (2) were seeded into replicate wells of 24 well dishes in the presence of the indicated concentrations (in ng/ml) of paclitaxel (A) or epothilone-B (B), allowed to grow for 7 d, and stained. Note that Tax-18 is unable to grow when no drug is present but its growth is rescued by both paclitaxel and epothilone-B. Compared to wild-type cells, Tax-18 is more resistant to the cytotoxic effects of both drugs.

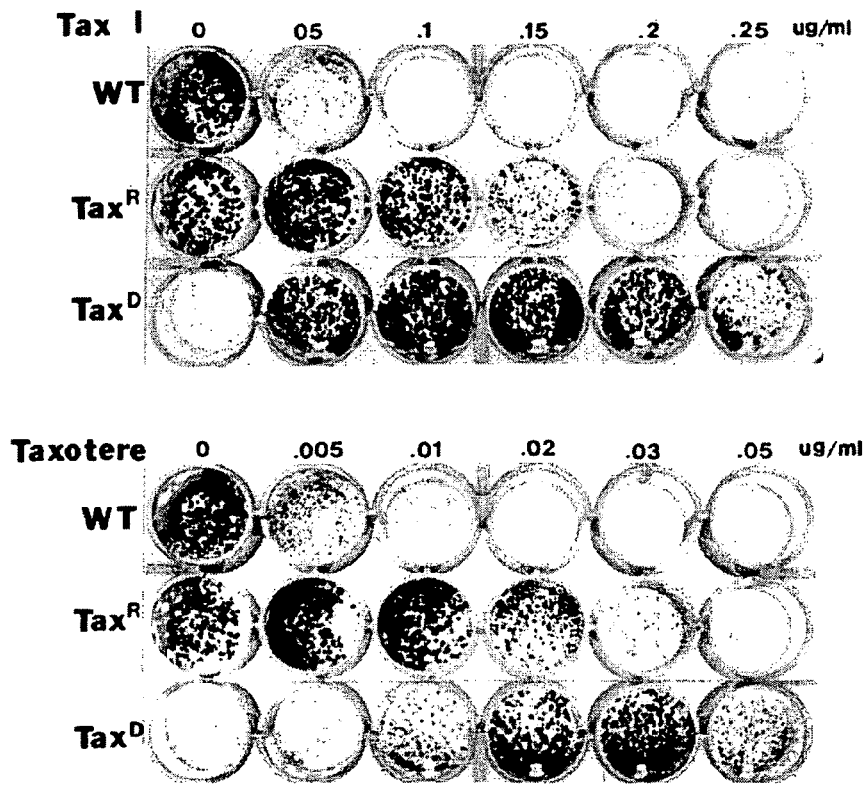

Fig. 10: Cross-resistance of Taxol resistant mutants to Taxotere. Wild-type CHO cells (WT), Taxol resistant mutant Tax 5-6 (Tax$^R$), and Taxol dependent mutant Tax 18 (Tax$^D$) were seeded into replicate wells of 24 well dishes at a density of approximately 100 cells per well in increasing concentrations of Taxol or Taxotere as indicated (in μg/ml). The cells were grown 7 days and then stained with methylene blue. Note that the Taxol resistant strain is more resistant to both Taxol and Taxotere compared to wild-type cells. Also note that the Taxol dependent mutant is unable to grow in the absence of drug but its growth is rescued by both drugs and the cells are resistant to both drugs.

```
M R E I V H I Q A G Q C G N Q I G A K F W E V I S D E H G I  30
D P T G T Y H G D S D L Q L D R I S V Y Y N E A T G G K Y V  60
P R A I L V D L E P G T M D S V R S G P F G Q I F R P D N F  90
V F G Q S G A G N N W A K G H Y T E G A E L V D S V L D V V  120
R K E A E S C D C L Q G F Q L T H S L G G G T G S G M G T L  150
L I S K I R E E Y P D R I M N T F S V V P S P K V S D T V V  180
E P Y N A T L S V H Q L V E N T D E T Y C I D N E A L Y D I  210
C F R T L K L T T P T Y G D L N H L V S A T M S G V T T C L  240
      A A A A                     A
        P   R                     F
        M                         H
        E
        F
        H
        R
```

```
R F P G Q L N A D L R K L A V N M V P F P R L H F F M P G F  270
A P L T S R G S Q Q Y R A L T V P E L T Q Q V F D A K N M M  300
A A C D P R H G R Y L T V A A V F R G R M S M K E V D E Q M  330
L N V Q N K N S S Y F V E W I P N N V K T A V C D I P P R G  360
L

ASSAY FOR THE DETECTION OF PACLITAXEL RESISTANT CELLS IN HUMAN TUMORS

This application claims the benefit of U.S. Provisional Application No. 60/135,047, filed May 20, 1999.

The United States government may own rights in the present invention pursuant to grant number CA052962 from the National Institutes of Health.

BACKGROUND OF THE INVENTION

Introduction

The present invention relates to purified drug resistant tumor cells, mutated polynucleotide sequences which confer drug resistance, an assay for detecting drug resistant tumor cells in mammals including human, reagents specific for PCR enhancement of mutant determinant polynucleotide sequences, and methods for treating patients afflicted with drug resistant tumor cells.

More particularly, this invention relates to an assay for detecting paclitaxel resistant tumor cells in humans using specific PCR primer polynucleotide sequences to selectively enhance and identify mutant genes from paclitaxel resistant tumor cells. This invention also relates to the specific polynucleotide primer sequences themselves, the specific mutant polynucleotide sequences and to methods for identifying paclitaxel resistant tumor cells and administering an effective amount of a secondary anti-tumor agent lethal to the identified paclitaxel resistant tumor cells.

Paclitaxel (Taxol), Taxotere and other paclitaxel-like drugs that are currently under development hold great promise for the treatment of human cancer. Paclitaxel has shown remarkable activity against breast and ovarian cancer, melanomas, non-small lung carcinoma, esophogeal cancer, Kaposi's sarcoma, and some hematological malignancies. It has been described as the most significant antitumor drug developed in the last several decades and will, without doubt, find widespread use in the treatment of cancer. However, as is true of virtually all cancer chemotherapeutic drugs, patients responsive to paclitaxel eventually relapse due to the emergence of drug resistant tumor cells.

Thus, there is a need in the art for methods to identify paclitaxel-resistant tumor cells, for agents that allow such identifications in a simple and cost effective way, and for methods for to treat patients with paclitaxel resistant tumor cells.

SUMMARY OF THE INVENTION

The present invention involves polynucleotide mutations which confer paclitaxel resistance; mutant cells which are paclitaxel resistant; and methods to determine paclitaxel resistance.

The present invention also provides a simple assay with sufficient sensitivity to detect drug resistant cells in tumor biopsies by extracting polynucleotide from the tissue. The extracted polynucleotide is then hybridized to mutant-specific PCR primers and the mutant regions of tubulin are identified by selective amplification. Once identified, a secondary treatment protocol can be administered to the patient to aid in tumor treatment.

DESCRIPTION OF THE DRAWINGS

The invention can be better understood with reference to the following detailed description together with the appended illustrative drawings in which like elements are numbered the same:

FIG. 1 depicts a mechanism to explain drug resistance in mutant CHO cells. The horizontal lines represent increasing stability and/or assembly (0 to 100%) of microtubules. It is postulated that cells can survive only within a narrow range of stability (the "normal range") and that wild type cells, on average, have microtubule stability near the center of this range. The bars represent the level of drug (the toxic doses) required to shift stability outside the normal range. Thus, a toxic dose of paclitaxel (solid bar) is the amount of drug that increases microtubule stability above "H", the high end of the normal range; while a toxic dose of colcemid (open bar) is the amount of drug needed to lower microtubule stability below "L", the low end of the normal range. Note that in colcemid resistant cells, the mutation confers increased microtubule stability so that the cells can tolerate higher concentrations of colcemid but the cells are more sensitive to paclitaxel. Conversely, in paclitaxel resistant cells, the mutation has destabilized microtubules such that cells tolerate higher concentrations of paclitaxel, but are sensitive to lower concentrations of colcemid. In paclitaxel dependent ($Tax^D$) cells, the mutation shifts microtubule stability below the normal range so that the cells cannot divide unless paclitaxel (or some other microtubule stabilizing agent) is added. This model is supported by direct measurements of microtubule assembly in mutant cell lines, and the mechanism of resistance has now gained wide acceptance (e.g., see Goodman & Gilman's "The Pharmacological Basis of Therapeutics," $9^{th}$ ed. P. 1261; and Pratt & Ruddon's "The Anticancer Drugs," $2^{nd}$ ed., p. 192).

FIG. 2 depicts an allele-specific amplification of β-tubulin DNA. PCR reactions were carried out on WT and mutant DNA that differ by a single mutation that changes leu217 (CTC) to arg (CGC). Each reaction contained a forward primer (β117f), a common reverse primer (β260r), and a WT (β217WTr) or mutant (β217 MUTr) allele-specific primer as indicated in the figure. (A): A diagram showing the relative positions of each primer on the DNA template. (B): The results of the PCR amplification. Upper band represents the control (β117f–β260r) amplification; lower band represents the allele specific (β117f–p217r) amplification. Note that the β217WTr primer amplifies WT but not mutant DNA, whereas the β217MUTr primer amplifies the mutant but not WT DNA. The β217WTr primer has a single 3' terminal mismatch (A:G) with the mutant DNA that is sufficient to prevent amplification. The β217MUTr primer has a 3' terminal mismatch (C:T) with WT DNA that is insufficient to prevent amplification. Therefore a second mismatch (C:A) was introduced at the third nucleotide from the 3' end (underlined in the sequence) to form the allele-specific primer. Note that a reduced amount of template was used for the PCR reaction in the third lane to demonstrate the necessity of including an in-tube control to normalize for problems during amplification.

FIG. 3 depicts two-dimensional gels of paclitaxel resistant CHO cell lines. Cells were labeled with $^{35}$S-methionine, lysed in a Triton X-100 containing buffer, and analyzed by two-dimensional gel electrophoresis. The tubulin containing region of the autoradiograms is shown. A, Tax-18. Wild-type CHO cells exhibit an identical pattern. B, Tax 2-4. This and several other mutants have an additional β-tubulin spot (arrowhead) that migrates with a more basic isoelectric point. C, Tax 11-3. This mutant is unique in exhibiting an additional β-tubulin spot (arrowhead) that migrates with a more acidic isoelectric point. The positions of α-tubulin (α), β-tubulin (β), and actin (a) are indicated in panel A.

FIG. 4 depicts immunofluorescence of CHO cells stably transfected with mutant HAβ1-tubulin cDNAs. Cells from strain tTApuro 6.6 were transfected with HAβ1 (A, B), HAβ1$_{L215H}$ (C, D), HAβ1$_{L217R}$ (E, F), or HAβ1$_{L228F}$ (G, H) cDNA. G418-resistant colonies were then selected and screened for production of the HA-tagged tubulin using immunofluorescence with an antibody specific for the HA tag. Examples of some of the positive clones are shown. The cells were either maintained in tetracycline throughout their growth (A, C, E, G), or they were incubated for 24 h in medium without tetracycline before analysis (B, D, F, H). Bar=10 μm.

FIG. 5 depicts production of wild-type and mutant HAβ1-tubulin in transfected cell lines. The stably transfected cell lines shown in FIG. 4 were maintained in tetracycline ("+" lanes) or were incubated 24 h in medium without tetracycline ("−"lanes) and cellular proteins were then resolved by SDS gel electrophoresis, transferred onto nitrocellulose, and probed with antibodies specific for α-tubulin and actin. Shown in the figure are cells transfected with HAβ1 (lanes 1 and 2), HAβ1$_{L215H}$ (lanes 3 and 4), HAβ1$_{L217R}$ (lanes 5 and 6), and HAβ1$_{L228F}$ (lanes 7 and 8). Note that the HA tag causes HAβ1-tubulin (HAβ) to migrate more slowly than edogenous β-tubulin (β). An antibody to actin was included to indicate relative protein loading.

FIG. 6 depicts cells expressing HAβ1$_{L215H}$ have reduced β-tubulin acetylation. A G418 selected population of cells transfected with HAβ1$_{L215H}$ cDNA was grown 24 h without tetracycline and stained for immunofluorescence with antibodies to the HA tag (A) and to acetylated β-tubulin (B). Small arrows indicate a cell that expressed the mutant HAβ1-tubulin. Large arrows indicate a neighboring cell that failed to express the mutant HAβ1-tubulin. Note that acetylation was greatly reduced in the cell that expressed the mutant HAβ1-tubulin. Bar=10 μm.

FIG. 7 depicts mutant HAβ1-tubulins confer paclitaxel resistance. Approximately 100 cells were seeded into replicate wells of 24-well dishes containing the indicated concentrations of paclitaxel (in ng/ml) with ("+") or without ("−") 1 μg/ml tetracycline. The cells were allowed to grow for 6–7 d and were then stained with methylene blue. The cell lines came from transfections with HAβ1 (A), HAβ1$_{L215H}$ (B), HAβ1$_{L217R}$ (C), or HAβ1$_{L228F}$ (D). Note that all cell lines had a similar sensitivity to the drug when cultured in the presence of tetracycline (no HAβ1-tubulin expression), but only the cells transfected with mutant forms of HAβ1-tubulin exhibited increased resistance to paclitaxel when cultured in the absence of tetracycline.

FIG. 8 depicts paclitaxel selects for transfected cells that express mutant HAβ1-tubulin. Cells transfected with HAβ1$_{L215H}$ cDNA were selected for resistance to G418 (A, B) or paclitaxel (C, D) either in the presence (A, C) or absence (B, D) of 1 μg/ml tetracycline. The total resistant cell population was then trypsinized and replated for 24 h in medium without tetracycline or paclitaxel before processing for immunofluorescence with an antibody specific for the HA tag. Arrows in B and C indicate cells that were positive for HAβ1$_{L215H}$-tubulin expression. Approximately 50% of the cells in panel A, and 100% of the cells in panel D were positive for expression. Bar=10 μm.

FIG. 9 shows paclitaxel resistant cells are cross resistant to epothilone-B. Cells from wild-type (1) or paclitaxel dependent cell line Tax-18 (2) were seeded into replicate wells of 24 well dishes in the presence of the indicated concentrations (in ng/ml) of paclitaxel (A) or epothilone-B (B), allowed to grow for 7 d, and stained. Note that Tax-18 is unable to grow when no drug is present but its growth is rescued by both paclitaxel and epothilone-B. Compared to wild-type cells, Tax-18 is more resistant to the cytotoxic effects of both drugs.

FIG. 10 illustrates cross-resistance of Taxol resistant mutants to Taxotere. Wild-type CHO cells (WT), Taxol resistant mutant Tax 5-6 (Tax$^R$), and Taxol dependent mutant Tax 18 (Tax$^D$) were seeded into replicate wells of 24 well dishes at a density of approximately 100 cells per well in increasing concentrations of Taxol or Taxotere as indicated (in μg/ml). The cells were grown 7 days and then stained with methylene blue. Note that the Taxol resistant strain is more resistant to both Taxol and Taxotere compared to wild-type cells. Also note that the Taxol dependent mutant is unable to grow in the absence of drug, but its growth is rescued by both drugs and the cells are resistant to both drugs.

FIG. 11 shows an amino acid sequence of mammalian beta-tubulin. The indicated amino acid sequence represents class 1 beta-tubulin (a ubiquitously expressed isotype) of mammalians such as rodents and humans. Below amino acids 214, 215, 216, 217 and 228 are single amino acid substitutions at those positions that have been shown to confer resistance to taxanes. Substitutions shown in bold were found in CHO cells directly selected for resistance to paclitaxel. Substitutions shown in italics were created by site-directed mutagenesis and demonstrated to confer resistance when cDNA was transfected into wild-type CHO cells.

DETAILED DESCRIPTION OF THE INVENTION

The inventors have found that the mutations that confer resistance to paclitaxel are clustered in a small region of β-tubulin (Table I). Of 9 identified mutant tubulins sequenced, 6 have a substitution at leu215, one has a substitution at leu217, and 2 have a substitution at leu228. The ability of 3 of these mutations to confer paclitaxel resistance has been confirmed by transfecting mutant DNAs into wild-type cells. The clustering of mutations all affecting leucines, is unusual and unexpected. The data support the hypothesis that the mutations affect a critical interaction between tubulin subunits that are involved in microtubule assembly and that the mechanism of paclitaxel is to facilitate this interaction. The hypothesis is consistent with data indicating the involvement of hydrophobic interactions in microtubule assembly.

TABLE I

Summary of β-Tubulin Mutations in Paclitaxel Resistant CHO Cells

| Cell line | Sequence[a] | β-tubulin alteration | % tubulin in polymer[b] | Resistant or Dependent[c] |
|---|---|---|---|---|
| Wild-type | -ACTCTCAAGCTCACC- SEQ ID 1 | None | 38% | |
| Tax 1–4 | -ACTACAAGCTCACC- SEQ ID 2 | L215H | 22% | R |
| Tax 2–4[d] | -ACTCACAAGCTCACC- SEQ ID 2 | L215H | 15% | D |
| Tax 4–9 | -ACTCACAAGCTCACC- SEQ ID 2 | L215H | 22% | R |
| Tax 1–19 | -ACTCGCAAGCTCACC- SEQ ID 3 | L215R | 29% | R |
| Tax 18 | -ACTTTTAAGCTCACC- SEQ ID 4 | L215F1 | 15% | D |
| Tax 6–21 | -ACTTTCAAGCTCACC- SEQ ID 5 | L215F2 | 15% | D |
| Tax 6–9 | -ACTCTCAAGCGCACC- SEQ ID 6 | L217R | 31% | R |
| Wild-type | -AACCACCTCGTCTCG- SEQ ID 7 | None | 38% | |
| Tax 11–3 | -AACCACTTCGTCTCG- SEQ ID 8 | L228F | 17% | D |
| Tax 2–5 | -AACCACCACGTCTCG- SEQ ID 9 | L228H | 19% | D |

[a]For the upper series of mutants, codons 215 and 217 are underlined. For the lower series, codon 228 is underlined. Mutations are indicated in bold letters.
[b]The fraction of total tubulin assembled into microtubules was determined as described in Ref. 13.
[c]R, cells are resistant to paclitaxel and grow without the drug. D, cells are resistant to paclitaxel but also require the continuous presence of the drug for cell division.
[d]Although this cell line has the same mutation as Tax 1–4 and Tax 4–9, its properties, including paclitaxel dependence, differ significantly from the other mutants. It is suspected that this cell line may have a second mutation in another gene because of its extremely low reversion frequency (Schibler, M., and Cabral, F. (1986) J. Cell Biol. 102, 1522–1531).

Because α-tubulin and β-tubulin are similar proteins, similar clustering of mutations are anticipated in α-tubulin in paclitaxel resistant cells and α-tubulin PCR mutant primer sequences can be constructed in a similar manner to the primers presented herein for β-tubulin in paclitaxel resistant tumor cells.

The assays of the present invention were performed using Chinese hamster ovary (CHO) cells selected for resistance to paclitaxel. It is important to note that human and hamster tubulin have identical amino acid sequences and the nucleotide sequences are highly homologous and the nucleotide differences do not alter the amino acid sequence, and therefore, the amino acid changes found in mutant CHO cells will also confer resistance in humans.

It has been established that the most frequent mechanism of resistance to paclitaxel occurs through mutations in tubulin that affect the stability of the microtubules. These paclitaxel-resistant cells assemble less microtubule polymer and are frequently hypersensitive to other drugs such as vinblastine and vincristine that inhibit microtubule assembly.

A model to explain these observations is provided in FIG. 1. The assay of the present invention can be used to identify many or most patients in danger of relapse due to tumor cell mutation and allow administration of alternate or additional treatment protocols using such agents as vinblastine or vincristine which are highly effective in eliminating the paclitaxel-resistant cells.

The identification of the mutations and the clustering of mutations within the tubulin genes provide the data to construct highly efficient assays to detect these mutations in patients. Until now, there has been no method available to easily detect paclitaxel resistant cells in human tumors. The present methods or assays involve the design and use of allele-specific oligonucleotide primers for PCR.

One such assay has been successfully confirmed for primers using the leu217 to arg mutation shown in FIG. 2. The wild-type primer (CTCCGTAGGTGGGCGTGGTGA (SEQ ID 10)) is able to amplify wild-type DNA; but because of a 3' mismatch with the mutant allele, it fails to amplify mutant DNA. Conversely, the mutant primer CTCCGTAG-GTGGGCGTGGCGC (SEQ ID 11) is able to amplify mutant DNA, but does not amplify the wild-type DNA because of 3' mismatch (underlined). The mutant primer also contains an intentional mismatch to both wild-type and mutant DNA at the third nucleotide from the 3' end (underlined) in order to enhance its allele specificity.

Thus, allele-specific primers covering most potential mutations can be used individually or a "cocktails" to detect the mutations in a single or very few PCR reactions. Alternatively, assays involving restriction enzyme digestion or allele-specific hybridization using the mutant DNA sequences can be used, but may lack the sensitivity and simplicity of the PCR assay.

The high frequency of mutations affecting only a few leucine residues of α-tubulin in paclitaxel-resistant mutants was unexpected. Currently, there is no rational basis for predicting how an individual patient will respond to paclitaxel therapy. An initial assay of the tumor for mutations in tubulin that confer paclitaxel resistance would help clinicians decide whether the patient is a good candidate for paclitaxel therapy and save needless morbidity with a treatment that is unlikely to be effective. It would also allow the clinician to choose an alternative or additional therapy at an early time in the disease progression, thereby enhancing the survival of the patient.

For patients that successfully respond to paclitaxel treatment, any tumor cells that reappear can be assayed at an early time for the presence of tubulin mutations, providing a rationale for changing the therapeutic regimen and helping decide which drugs should be used for the new therapy. For example, tumors that are positive in the assay will have cells that are resistant to paclitaxel because of mutations that affect microtubule stability. These tumors would be good candidates for treatment with vinblastine or vincristine, since many such cells are hypersensitive to these drugs. On the other hand, if the cells fail to exhibit the mutations, they might have the multidrug resistance phenotype and would be candidates for treatment with drugs that are not hydrophobic such as DNA alkylating agents, antimetabolites, or similar agents.

The sensitivity of the PCR assay can be determined with the primers for the leu217 mutation in CHO cells. The sensitivity greatly depends on the number of primers in the "cocktail" used for the assay, the relative abilities of these primers to discriminate wild-type from mutant DNA, and the heterogeneity of the tissue removed from the patient.

Mammals express 6 α- and 6 β-tubulin genes, which are the targeted genes. To further optimize assays, it may be necessary to determine which tubulin isotype is involved in paclitaxel resistance for each type of tumor in certain instances. The tubulin is expressed in a tissue specific manner, with some forms restricted to certain tissues, which are widely disclosed in the prior art literature. Furthermore, the present inventors have found in CHO cells that the most abundant tubulin isotype is the one always involved in conferring resistance, which was completely unexpected. Thus, one skilled in the art must merely find the most abundant isotype for each type of tumor, which is disclosed in many technical journal and prior art references.

Paclitaxel is the prototype for a novel class of agents that inhibit cells in mitosis by promoting and stabilizing microtubule assembly. Early studies with this compound demonstrated that it binds to microtubules in a 1:1 stoichiometry with tubulin heterodimers (Manfredi, J. J., Parness, J., and Horwitz, S. B. (1981) *J. Cell Biol.* 94, 688–696) and inhibits microtubule disassembly. It is also able to induce microtubule assembly both in vitro and in vivo and induces microtubule bundle formation in treated cells (Schiff, P. B., Fant, J., and Horwitz, S. B. (1979) *Nature* 277, 665–667 and Schiff, P. B., and Horwitz, S. B. (1980) *Proc. Natl. Acad. Sci. U.S.A.* 77, 1561–1565). Recent interest in this and related compounds has been fueled by clinical studies demonstrating remarkable activity of paclitaxel against a number of malignant diseases (Rowinsky, E. K., and Donehower, R. C. (1995) *N. E. J. Med.* 332, 1004–1014). Although still in clinical trials, the demonstrated activity of paclitaxel in phase II studies has led to FDA approval for its use in refractory cases of breast and ovarian cancer. As more patients are treated with this drug, clinical resistance is expected to become an increasingly significant problem.

The mechanisms by which tumor cells acquire resistance to paclitaxel are not fully understood. Cell culture studies have shown that paclitaxel is a substrate for the multidrug resistance pump (gP170), and cells selected for high levels of resistance to the drug have increased gP170 (Casazza, A. M., and Fairchild, C. R. (1996) *Cancer Treatment & Research* 87, 149–71). Nevertheless, it has yet to be demonstrated that this mechanism is significant in paclitaxel refractory tumors. Indeed, the remarkable efficacy of paclitaxel in early clinical studies of patients who were pretreated with Adriamycin, a well known substrate for gP170, argues that the multidrug resistance (mdr) phenotype may not be as clinically prevalent as had initially been anticipated (Schiff, P. B., and Horwitz, S. B. (1980) *Proc. Natl. Acad. Sci. U.S.A.* 77, 1561–1565).

Additional mechanisms of resistance to paclitaxel have been reported. For example, several laboratories have provided evidence that changes in the expression of specific β-tubulin genes are associated with paclitaxel resistance in cultured tumor cell lines (Haber, M., Burkhart, C. A., Regl, D. L., Madafiglio, J., Norris, M. D., and Horwitz, S. B. (1995) *J. Biol. Chem.* 270, 31269–75; Jaffrezou, J. P., Dumontet, C., Derry, W. B., Duran, G., Chen, G., Tsuchiya, E., Wilson, L., Jordan, M. A., and Sikic, B. I. (1995) *Oncology Res.* 7, 517–27; Kavallaris, M., Kuo, D. Y. S., Burkhart, C. A., Regl, D. L., Norris, M. D., Haber, M., and Horwitz, S. B. (1997) *J. Clin. Invest.* 100, 1282–93; and Ranganathan, S., Dexter, D. W., Benetatos, C. A., and Hudes, G. R. (1998) *Biochim. Biophys. Acta* 1395, 237–245). More recently, a report describing mutations in β-tubulin that make the protein unresponsive to paclitaxel has appeared (Giannakakou, P., Sackett, D. L., Kang, Y.-K., Zhan, Z., Buters, J. T. M., Fojo, T., and Poruchynsky, M. S. (1997) *J. Biol. Chem.* 272, 17118–17125). To date, however, there is little evidence that any of the mechanisms described in cell culture cause paclitaxel resistance in human tumors.

The inventor's own studies have described a resistance mechanism mediated by tubulin alterations that affect microtubule assembly (Cabral, F., and Barlow, S. B. (1991) *Pharmac. Ther.* 52, 159–171). Based on mutant properties and drug cross-resistance patterns, it is proposed that these changes in microtubule assembly could compensate for the presence of the drug (Cabral, F., Brady, R. C., and Schibler, M. J. (1986) *Ann. N.Y. Acad. Sci.* 466, 745–756). The inventors were later able to directly demonstrate that paclitaxel resistant Chinese hamster ovary (CHO) cells have diminished microtubule assembly compared to wild-type controls (Minotti, A. M., Barlow, S. B., and Cabral, F. (1991) *J. Biol. Chem.* 266, 3987–3994). Thus, isolation of paclitaxel resistant mutants provides an opportunity to study mutations that not only give information about the mechanisms of drug action and resistance, but also give structural information about regions of tubulin that are involved in assembly.

The inventors have now sequenced 9 mutant β-tubulin alleles and find that the mutations cluster at a site that is likely to be involved in lateral or longitudinal interactions during microtubule assembly. Remarkably, these mutations are present in the H6H7 region of of tubulin. Previously, it was believed that this region was not associated with paclitaxel binding. However, the inventors have isolated mutants in the H6H7 region, which are directly related to paclitaxel resistence.

There is some significance to the fact that all the mutated residues are leucines—it certainly indicates that the changes that produce taxol resistance are not random. One possibility is that the leucines define a structural motif (e.g., analogous to a leucine zipper, but clearly distinct) that forms an interaction site with a neighboring subunit. A more trivial explanation is that the leucines are among the least critical residues in the region and are therefore better able to tolerate changes that produce the kind of subtle alterations in tubulin assembly that give resistance to taxol. The fact that the 3 leucines are highly conserved throughout all species and that the conservation extends to alpha and even gamma tubulin would tend to argue for the former alternative, but it will take a lot of further experimentation before the true significance can be elucidated.

All 3 leucines in hamster are encoded by a CTC. Thus, a single base change can lead to substitution of histidine, arginine, phenylalanine, isoleucine, valine, or proline. Only his, arg, and phe were isolated in the mutant cell lines. By transfection of cDNA altered by site-directed mutagenesis, is has been found that ile and val do not produce taxol resistance, probably because they do not perturb the structure of the microtubule sufficiently to produce resistance. Proline substitution can cause resistance, but appears to do so when expressed at very low levels. Moreover, the inventors have not been able to express it at high levels. This suggests that pro was not isolated in the mutant cell lines because it disrupts the structure of microtubules too severely for the cells to survive.

The codons for leucine in human DNA are CTG at positions 215 and 217, and CTT at position 228. Single nucleotide changes will produce the same amino acid substitutions at 228, but a different set (valine, methionine, glutamine, arginine, or proline) at 215 and 217. Thus, 2 new possibilities (methionine and glutamine) might be found at 215 or 217 in human cells resistant to taxol. Of the two, methionine has been tested by transfection and it turns out to produce borderline resistance even at high levels of expression. A glutamine substitution has not yet been tested and should therefore be considered a presumptive candidate for producing resistance.

Unless otherwise stated, the following terms shall have the following meanings:

The term "primer" denotes a specific oligonucleotide sequence that is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., PNA as defined hereinbelow) which can be used to identify a specific polynucleotide present in samples bearing the complementary sequence.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as methylation or capping and unmodified forms of the polynucleotide. The terms "polynucleotide," "oligomer," "oligonucleotide," and "oligo" are used interchangeably herein.

The term "isolated" means that the material is removed from its original environment (e.g., the natural environment if it is naturally occurring). For example, a naturally occurring polynucleotide or polypeptide present in a living animal is not isolated, but the same polynucleotide or DNA or polypeptide that is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Recombinant host cells," "host cells," "cells," "cell lines," "cell cultures," and other such terms denoting microorganisms or higher eukaryotic cell lines cultured as unicellular entities refer to cells that can be, or have been, used as recipients for recombinant vector or other transferred DNA, and include the original progeny of the original cell that has been transfected.

As used herein "replicon" means any genetic element, such as a plasmid, a chromosome or a virus, that behaves as an autonomous unit of polynucleotide replication within a cell.

The term "mammal" is defined as any class of warm-blooded higher vertebrates that includes humans.

A "vector" is a replicon in which another polynucleotide segment is attached, such as to bring about the replication and/or expression of the attached segment.

The term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

The term "open reading frame" or "ORF" refers to a region of a polynucleotide sequence that encodes a polypeptide. This region may represent a portion of a coding sequence or a total coding sequence.

A "coding sequence" is a polynucleotide sequence that is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA and recombinant polynucleotide sequences.

"Tumor" or "tumor cell" is defined as an abnormal benign or malignant mass of tissue that is not inflamatory, arising without cause from cells of pre-existant tissue, and possesses no physiological function.

A "non-paclitaxel oncologic medication" is defined as medications that do not stabilize microtubule assembly but act against the tumor cell via some other mechanism, such as weakening microtubule assembly, for example vinblastine and vincristine.

"Multidrug resistance (MDR)" could potentially refer to any mechanism that confers resistance to many drugs simultaneously, but the term is generally reserved for a specific mechanism that limits the ability of a broad class of hydrophobic, weakly cationic compounds to accumulate in the cell. These compounds have diverse structures and mechanisms of action yet all are affected by this mechanism. Recent work has shown that a family of ATP driven pumps are responsible for this phenomenon, but the first and most familiar member of this family is P-glycoprotein. This protein sits in the plasma membrane and acts as a broad specificity "pump" that extrudes the drugs from the cell. Most of the known antimitotic drugs (that affect microtubule assembly) are affected by P-glycoprotein mediated MDR, but there are now a number of synthetic and natural compounds that inhibit or promote microtubule assembly but are not affected by MDR.

"Taxol" refers to a specific drug first developed by the scientific community with the support of NIH, but now marketed exclusively by Bristol Meyer Squibb, that now is called by its generic name of "paclitaxel". It is a natural product that is found in highest abundance in the bark of the western yew tree. A related drug, "Taxotere", was created by chemical synthesis starting with a precursor derived from the leaves of a shrub that is a member of the same family as the western yew. That drug is marketed by Rhone Poulenc. In addition, there are now a number of synthetic analogs of taxol and taxotere that also promote microtubule assembly. All of these drugs (including taxol and taxotere) are classified as "taxanes." More recently, new drugs with a taxol-like action have been discovered. These include the natural products epothilones, discodermolide, and a number of synthetic compounds being developed by a variety of pharmaceutical companies and independent research laboratories. New ones are being described almost daily. Because the mechanism the inventors' have described in the CHO mutants counters the effect of all these drugs of diverse structure, the mutations can confer resistance to all "paclitaxel-like drugs" or "drugs which stabilize microtubule assembly" including taxanes, epothilones, discodermolide, new analogs, or any yet-to-be-discovered agents that act by promoting the assembly of microtubules.

As used herein, "epitope" means an antigenic determinant of a polypeptide or protein. Conceivably, an epitope can comprise three amino acids in a spatial conformation that is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

"H6H7" region is defined as the amino acid sequence encompassing helix 6 of tubulin, helix7 of tubulin, and the loop that connects the two helices.

"Wild-type" is described as the genotype that naturally occurs in the normal population wherein no resistance to paclitaxel-like drugs is experienced. For an amino acid sequence it represents the wild-type Table I as "wild-type" in the first and ninth row as well as described in FIG. 11.

"Analog" is defined as a compound that resembles another in function and/or function.

The term "test sample" refers to a component of an individual's body that is the source of the analyte (such as antibodies of interest or antigens of interest). These components are well known in the art. A test sample is typically anything suspected of containing a target sequence. Test samples can be prepared using methodologies well known in the art such as by obtaining a specimen from an individual and, if necessary, disrupting any cells contained thereby to release target nucleic acids. These test samples include biological samples that can be tested by the methods of the present invention described herein and include human and animal body fluids such as whole blood, serum, plasma, cerebrospinal fluid, sputum, bronchial washing, bronchial aspirates, urine, lymph fluids, and various external secretions of the respiratory, intestinal and genitourinary tracts, tears, saliva, milk, white blood cells, myelomas and the like; biological fluids such as cell culture supernatants; tissue specimens that may be fixed; and cell specimens that may be fixed.

The present invention provides assays that utilize specific binding members. A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

Specific binding members include "specific binding molecules." A "specific binding molecule" intends any specific binding member, particularly an immunoreactive specific binding member. As such, the term "specific binding molecule" encompasses antibody molecules (obtained from both polyclonal and monoclonal preparations), as well as, the following: hybrid (chimeric) antibody molecules (see, for example, Winter, et al., *Nature* 349:293–299 (1991), and U.S. Pat. No. 4,816,567); F(ab')$_2$ and F(ab) fragments; Fv molecules (non-covalent heterodimers, see, for example, Inbar, et al., *Proc. Natl. Acad. Sci. USA* 69:2659–2662 (1972), and Ehrlich, et al., *Biochem.* 19:4091–4096 (1980)); single chain Fv molecules (sFv) (see, for example, Huston, et al., *Proc. Natl. Acad. Sci. USA* 85:5879–5883 (1988)); humanized antibody molecules (see, for example, Riechmann, et al., *Nature* 332:323–327 (1988), Verhoeyan, et al., *Science* 239:1534–1536 (1988), and UK Patent Publication NO. GB 2,276,169, published 21 Sep. 1994); and, any functional fragments obtained from such molecules, wherein such fragments retain immunological binding properties of the parent antibody molecule.

A "capture reagent," as used herein, refers to an unlabeled specific binding member that is specific either for the analyte as in a sandwich assay, for the indicator reagent or analyte as in a competitive assay, or for an ancillary specific binding member, that itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") that is capable of generating and generates a measurable signal detectable by external means, conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements and direct visual labels. Examples of enzymes include alkaline phosphatase, horseradish peroxidase, beta-galactosidase and the like. The selection of a particular label is not critical, but it must be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, sheep (or other animal) red blood cells and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material that is insoluble, or can be made insoluble by a subsequent reaction. The solid phase can be chosen for its intrinsic ability to attract and immobilize the capture reagent. Alternatively, the solid phase can retain an additional receptor that has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member that is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

Reagents.

The present invention provides reagents such as polynucleotide sequences derived from a paclitaxel resistant cell, polypeptides encoded thereby and antibodies specific for these polypeptides. The present invention also provides reagents such as oligonucleotide fragments derived from the disclosed polynucleotides and nucleic acid sequences complementary to these polynucleotides. The polynucleotides, polypeptides, or antibodies of the present invention may be used to provide information leading to the detecting, diagnosing, staging, monitoring, prognosticating, in vivo imaging, preventing or treating of, or determining the predisposition to, cancer and drug resistance. The sequences disclosed herein represent unique polynucleotides that can be used in assays or for producing a specific profile of gene transcription activity. Such assays are disclosed in European Patent Number 0373203B1 and International Publication No. WO 95/11995, which are hereby incorporated by reference.

Selected polynucleotides can be used in the methods described herein for the detection of normal or altered gene expression. Such methods may employ mutated or wild-type polynucleotides or oligonucleotides, fragments or derivatives thereof, or nucleic acid sequences complementary thereto.

The polynucleotides disclosed herein, their complementary sequences, or fragments of either, can be used in assays to detect, amplify or quantify genes, nucleic acids, cDNAs or mRNAs relating to paclitaxel resistance and conditions associated therewith such as MDR. They also can be used to identify an entire or partial coding region of a polypeptide. They further can be provided in individual containers in the form of a kit for assays, or provided as individual compositions. If provided in a kit for assays, other suitable reagents such as buffers, conjugates and the like may be included.

The polynucleotide may be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence that coding sequence, as a result of the redundancy or degeneracy of the genetic code, encodes the same polypeptide as the DNA provided herein.

This polynucleotide may include only the coding sequence for the polypeptide, or the coding sequence for the polypeptide and an additional coding sequence such as a leader or secretory sequence or a proprotein sequence, or the coding sequence for the polypeptide (and optionally an additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence that is a naturally occurring allelic variant of the coding sequence provided herein.

In addition, the coding sequence for the polypeptide may be fused in the same reading frame to a polynucleotide sequence that aids in expression and secretion of a polypeptide from a host cell, for example, a leader sequence that functions as a secretory sequence for controlling transport of a polypeptide from the cell. The polypeptide having a leader sequence is a preprotein and may have the leader sequence cleaved by the host cell to form the polypeptide. The polynucleotides may also encode for a proprotein that is the protein plus additional 5' amino acid residues. A protein having a prosequence is a proprotein and may, in some cases, be an inactive form of the protein. Once the prosequence is cleaved, an active protein remains. Thus, the polynucleotide of the present invention may encode for a protein, or for a protein having a prosequence, or for a protein having both a presequence (leader sequence) and a prosequence.

The polynucleotides of the present invention may also have the coding sequence fused in frame to a marker sequence that allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. a COS-7 cell line, is used. The HA tag corresponds to an epitope derived from the influenza hemagglutinin protein. See, for example, I. Wilson et al., *Cell* 37:767 (1984).

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. In one embodiment of the present invention, a nucleic acid molecule is capable of hybridizing selectively to a target sequence under moderately stringent hybridization conditions. In the context of the present invention, moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press). Hybrid molecules can be formed, for example, on a solid support, in solution, and in tissue sections. The formation of hybrids can be monitored by inclusion of a reporter molecule, typically, in the probe. Such reporter molecules, or detectable elements include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well within the skill of the routineer in the art (see, for example, Sambrook, et al., *Molecular Cloning: A Laboratory Manual*, Second Edition, (1989) Cold Spring Harbor, N.Y.).

"Stringent conditions" are defined as conditions that employ low ionic strength and high temperature for washing, for example, 0.015 M NaCl/0.015 M sodium citrate (SSC); 0.1% sodium lauryl sulfate (SDS) at 50 degrees C., or (2) employ a denaturing agent such as formamide during hyridization, e.g. 50% formamide with 0.1% bovine serum albumen/0.1% Ficoll/0.1% polyvinylpyrrolidone/50 mM sodium phosphate buffer at pH 6.5 with 750 mM NaCl, 75 mM sodium citrate at 42 degrees C.

The present invention also provides an antibody produced by using a purified polypeptide of which at least a portion of the polypeptide is encoded by a polynucleotide selected from the polynucleotides provided herein. These antibodies may be used in the methods provided herein for the detection of antigen in test samples. The presence of antigen in the test samples is indicative of the presence of a breast disease or condition. The antibody also may be used for therapeutic purposes, for example, in neutralizing the activity of polypeptide in conditions associated with altered or abnormal expression.

The present invention further relates to a polypeptide that has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention. The polypeptides and polynucleotides of the present invention are provided preferably in an isolated form and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in fluorescent in situ hybridization (FISH) technology to perform chromosomal analysis, and used to identify cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in tissue specimens or cells.

This invention also provides teachings as to the production of the polynucleotides and polypeptides provided herein.

Probe Assays

The sequences provided herein may be used to produce probes that can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multi-gene family or in related species like mouse and man.

The polymerase chain reaction (PCR) is a technique for amplifying a desired nucleic acid sequence (target) contained in a nucleic acid or mixture thereof. In PCR, a pair of primers is employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used that include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes that can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A439 182 to K. Backman et al., published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, that is incorporated herein by reference; or reverse transcribe mRNA into cDNA followed by asymmetric gap ligase chain reaction (RT-AGLCR) as described by R. L. Marshall et al., *PCR Methods and Applications* 4:80–84 (1994), which also is incorporated herein by reference.

Other known amplification methods that can be utilized herein include but are not limited to the so-called "NASBA" or "3SR" technique described by J. C. Guatelli et al., *Proc. Natl. Acad. Sci. USA* 87:1874–1878 (1990) and also described by J. Compton, *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 [1996]) and European Patent Application No. 684315; and target mediated amplification, as described in International Publication No. WO 93/22461.

Detection of mutations to paclitaxel-like drugs may be accomplished using any suitable detection method, including those detection methods that are currently well known in the art, as well as detection strategies that may evolve later. Examples of the foregoing presently known detection methods are hereby incorporated herein by reference. See, for example, Caskey et al., U.S. Pat. No. 5,582,989, Gelfand et al., U.S. Pat. No. 5,210,015. Examples of such detection methods include target amplification methods as well as signal amplification technologies. An example of presently known detection methods would include the nucleic acid amplification technologies referred to as PCR, LCR, NASBA, SDA, RCR and TMA. See, for example, Caskey et al., U.S. Pat. No. 5,582,989, Gelfand et al., U.S. Pat. No. 5,210,015. All of the foregoing are hereby incorporated by reference. Detection may also be accomplished using signal amplification such as that disclosed in Snitman et al., U.S. Pat. No. 5,273,882. While the amplification of target or signal is preferred at present, it is contemplated and within the scope of the present invention that ultrasensitive detection methods that do not require amplification can be utilized herein.

Detection, both amplified and non-amplified, may be performed using a variety of heterogeneous and homogeneous detection formats. Examples of heterogeneous detection formats are disclosed in Snitman et al., U.S. Pat. No. 5,273,882, Albarella et al., in EP-84114441.9, Urdea et al., U.S. Pat. No. 5,124,246, Ullman et al. U.S. Pat. No. 5,185,243 and Kourilsky et al., U.S. Pat. No. 4,581,333. All of the foregoing are hereby incorporated by reference. Examples of homogeneous detection formats are disclosed in, Caskey et al., U.S. Pat. No. 5,582,989, Gelfand et al., U.S. Pat. No. 5,210,015, which are incorporated herein by reference. Also contemplated and within the scope of the present invention is the use of multiple probes in the hybridization assay, which use improves sensitivity and amplification of the BS325 signal. See, for example, Caskey et al., U.S. Pat. No. 5,582,989, Gelfand et al., U.S. Pat. No. 5,210,015, which are incorporated herein by reference.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method provided herein are labeled with capture and detection labels, wherein probes are labeled with one type of label and primers are labeled with another type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences generally are selected to be shorter than the primer sequences and therefore have a lower melt temperature than the primers. Accordingly, the melt temperature of the amplicon produced by the primers should also have a higher melt temperature than the probes. Thus, as the mixture cools, the reformation of the double stranded amplicon would be expected. As previously stated, however, this is not the case. The probes are found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate that generally comprises a binding member attached to a directly detectable label. The conjugate becomes bound to the complexes and the conjugate's presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

In one embodiment, the heterogeneous assays can be conveniently performed using a solid phase support that carries an array of nucleic acid molecules. Such arrays are useful for high-throughput and/or multiplexed assay formats. Various methods for forming such arrays from preformed nucleic acid molecules, or methods for generating the array using in situ synthesis techniques, are generally known in the art. (See, for example, Dattagupta, et al., EP Publication No. 0 234, 726A3; Southern, U.S. Pat. No. 5,700,637; Pirrung, et al., U.S. Pat. No. 5,143,854; PCT International Publication No. WO 92/10092; and, Fodor, et al., Science 251:767–777 (1991)).

Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well-known amplification reactions that include thermal cycle reaction mixtures, particularly in PCR and gap LCR (GLCR). Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation that utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated, they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers that are complementary to a portion of a target strand and its complement are employed in PCR. For LCR, four probes, two of which are complementary to a target sequence and two of which are similarly complementary to the target's complement, are generally employed. In addition to the primer sets and enzymes previously mentioned, a nucleic acid amplification reaction mixture may also comprise other reagents that are well known and include but are not limited to: enzyme cofactors such as manganese; magnesium; salts; nicotinamide adenine dinucleotide (NAD); and deoxynucleotide triphosphates (dNTPs) such as, for example, deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids that are disclosed in International Publication No. WO 92/20702; morpholino analogs that are described in U.S. Pat. Nos. 5,185,444, 5,034,506 and 5,142,047; and the like. Depending upon the type of label carried by the probe, the probe is employed to capture or detect the amplicon generated by the amplification reaction. The probe is not involved in amplification of the target sequence and therefore may have to be rendered "non-extendible" in that additional dNTPs cannot be added to the probe. In and of themselves, analogs usually are non-extendible and nucleic acid probes can be rendered non-extendible by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications that can be used to render a probe non-extendible. The ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), DuPont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe-labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 and 630,908, filed Dec. 20, 1990, which are each incorporated herein by reference, teach methods for labeling probes at their 5' and 3' termini, respectively. International Publication Nos WO 92/10505, published 25 Jun. 1992, and WO 92/11388, published 9 Jul. 1992, teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46):5905–5908 (1988); or J. S. Cohen et al., published U.S. patent application Ser. No. 07/246,688 (NTIS ORDER No. PAT-APPL-7–246,688) (1989). Preferably, probes are labeled at their 3' and 5' ends.

A capture label is attached to the primers or probes and can be a specific binding member, which forms a binding pair with the solid phase reagent's specific binding member. It will be understood that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides, wherein at least one polynucleotide is a BS325 molecule as described herein, hybridizing the test sample with the plurality of polynucleotides and detecting hybridization complexes. Hybridization complexes are identified and quantitated to compile a profile that is indicative of breast tissue disease, such as breast cancer. Expressed RNA sequences may further be detected by reverse transcription and amplification of the DNA product by procedures well known in the art, including polymerase chain reaction (PCR).

Drug Screening.

The present invention also provides a method of screening a plurality of compounds for specific binding to the mutated polypeptide(s), or any fragment thereof, to identify at least one compound that specifically binds the mutated polypeptide. Such a method comprises the steps of providing at least one compound; combining the polypeptide with each compound under suitable conditions for a time sufficient to allow binding; and detecting the polypeptide binding to each compound.

The polypeptide or peptide fragment employed in such a test may either be free in solution, affixed to a solid support, borne on a cell surface or located intracellularly. One method of screening utilizes eukaryotic or prokaryotic host cells that are stably transfected with recombinant nucleic acids, which can express the polypeptide or peptide fragment. A drug, compound, or any other agent may be screened against such transfected cells in competitive binding assays. For example, the formation of complexes between a polypeptide and the agent being tested can be measured in either viable or fixed cells.

The present invention thus provides methods of screening for drugs, compounds, or any other agent, which can be used to treat resistant diseases associated with these mutations. These methods comprise contacting the agent with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is used as a measure of the ability of the particular agent to bind to the polypeptide or to interfere with the polypeptide/cell complex.

The present invention also encompasses the use of competitive screening assays in which neutralizing antibodies capable of binding polypeptide specifically compete with a test agent for binding to the polypeptide or fragment thereof. In this manner, the antibodies can be used to detect the presence of any polypeptide in the test sample that shares one or more antigenic determinants with a mutated polypeptide as provided herein.

Another technique for screening provides high throughput screening for compounds having suitable binding affinity to at least one polypeptide disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well known in the art. Purified polypeptide can also be coated directly onto plates for use in the screening techniques described herein. In addition, non-neutralizing antibodies can be used to capture the polypeptide and immobilize it on the solid support. See, for example, EP 84/03564, published on Sep. 13, 1984, that is incorporated herein by reference.

The goal of rational drug design is to produce structural analogs of biologically active polypeptides of interest or of the small molecules including agonists, antagonists, or inhibitors with which they interact. Such structural analogs can be used to design drugs that are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J. Biochem. (Tokyo)* 113 (6):742–746 (1993), incorporated herein by reference.

It also is possible to isolate a target-specific antibody selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then can be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence that is derivable from the nucleic acid sequence provided herein will provide guidance to those employing computer modeling techniques in place of, or in addition to, x-ray crystallography.

The present invention also is directed to antagonists and inhibitors of the polypeptides of the present invention. The antagonists and inhibitors are those, which inhibit or eliminate the function of the polypeptide. Thus, for example, an antagonist may bind to a polypeptide of the present invention and inhibit or eliminate its function. The antagonist, for example, could be an antibody against the polypeptide, which eliminates the activity of a mutant polypeptide by binding a mutant polypeptide, or in some cases the antagonist may be an oligonucleotide. Examples of small molecule inhibitors include, but are not limited to, small peptides or peptide-like molecules.

The antagonists and inhibitors may be employed as a composition with a pharmaceutically acceptable carrier including, but not limited to, saline, buffered saline, dextrose, water, glycerol, ethanol and combinations thereof. Administration of polypeptide inhibitors is preferably systemic. The present invention also provides an antibody that inhibits the action of such a polypeptide.

Recombinant Technology.

The present invention provides host cells and expression vectors comprising mutated polynucleotides of the present invention and methods for the production of the polypeptide(s) they encode. Such methods comprise culturing the host cells under conditions suitable for the expression of the mutant polynucleotide and recovering the mutant polypeptide from the cell culture.

The present invention also provides vectors that include mutant polynucleotides of the present invention, host cells that are genetically engineered with vectors of the present invention and the production of polypeptides of the present invention by recombinant techniques.

Host cells are genetically engineered (transfected, transduced or transformed) with the vectors of this invention, which may be cloning vectors or expression vectors. The vector may be in the form of a plasmid, a viral particle, a phage, etc. The engineered host cells can be cultured in conventional nutrient media modified as appropriate for activating promoters, selecting transfected cells, or amplifying BS325 gene(s). The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, the polynucleotide sequence may be included in any one of a variety of expression vehicles, in particular, vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, the LTR or the SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transfected host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transfect an appropriate host to permit the host to express the protein. As representative examples of appropriate hosts, there may be mentioned: bacterial cells, such as E. coli, Salmonella typhimurium; Streptomyces sp.; fungal cells, such as yeast; insect cells, such as Drosophila and Sf9; animal cells, such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences including, for example, a promoter, operably linked to the sequence. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia); Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retroviruses and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation [L. Davis et al., Basic Methods in Molecular Biology, 2nd edition, Appleton and Lang, Paramount Publishing, East Norwalk, Conn. (1994)].

The constructs in host cells can be used in a conventional manner to produce the gene product encoded by the recombinant sequence. Alternatively, the polypeptides of the invention can be synthetically produced by conventional peptide synthesizers.

Recombinant proteins can be expressed in mammalian cells, yeast, bacteria, or other cells, under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, (Cold Spring Harbor, N.Y., 1989), which is hereby incorporated by reference.

Transcription of a DNA encoding the polypeptide(s) of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin and adenovirus enhancers.

Generally, recombinant expression vectors will include origins of replication and selectable markers permitting transfection of the host cell, e.g., the ampicillin resistance gene of E. coli and S. cerevisiae TRP1 gene, and a promoter derived from a highly expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transfection include E. coli, Bacillus subtilis, Salmonella typhimurium and various species within the genera Pseudomonas, Streptomyces and Staphylococcus, although others may also be employed as a routine matter of choice.

Useful expression vectors for bacterial use comprise a selectable marker and bacterial origin of replication derived from plasmids comprising genetic elements of the well known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transfection of a suitable host and growth of the host to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method including freeze-thaw cycling, sonication, mechanical disruption, or use of cell lysing agents. Such methods are well known to the ordinary artisan.

Various mammalian cell culture systems can also be employed to express recombinant protein. Examples of mammalian expression systems include the COS-7 lines of monkey kidney fibroblasts described by Gluzman, *Cell* 23:175 (1981), and other cell lines capable of expressing a compatible vector, such as the C127, HEK-293, 3T3, CHO, HeLa and BHK cell lines. Mammalian expression vectors will comprise an origin of replication, a suitable promoter and enhancer and also any necessary ribosome binding sites, polyadenylation sites, splice donor and acceptor sites, transcriptional termination sequences and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

Polypeptides are recovered and purified from recombinant cell cultures by known methods including affinity chromatography, ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification [Price, et al., *J. Biol. Chem.* 244:917 (1969)]. Protein refolding steps can be used, as necessary, in completing configuration of the polypeptide. Finally, high performance liquid chromatography (HPLC) can be employed for final purification steps.

Thus, polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to one of ordinary skill in the art.

The following is the general procedure for the isolation and analysis of cDNA clones. In a particular embodiment disclosed herein, mRNA is isolated from tissue and used to generate the cDNA library. Tissue is obtained from patients by surgical resection and is classified as tumor or non-tumor tissue by a pathologist.

Methods for DNA sequencing are well known in the art. Conventional enzymatic methods employ DNA polymerase, Klenow fragment, Sequenase (U.S. Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while other reading frames tend to contain numerous stop codons. In such cases, reading frame determination is straightforward. In other more difficult cases, further analysis is required.

Algorithms have been created to analyze the occurrence of individual nucleotide bases at each putative codon triplet. See, for example J. W. Fickett, *Nuc. Acids Res.* 10:5303 (1982). Coding DNA for particular organisms (bacteria, plants and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well-established recombinant DNA techniques. See J. Sambrook et al., supra. Vectors of interest include cloning vectors, such as plasmids, cosmids, phage derivatives, phagemids, as well as sequencing, replication and expression vectors, and the like. In general, such vectors contain an origin of replication functional in at least one organism, convenient restriction endonuclease digestion sites and selectable markers appropriate for particular host cells. The vectors can be transferred by a variety of means known to those of skill in the art into suitable host cells that then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel et al., *Current Protocols in Molecular Biology*, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and, as such, may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequences.

Expression of a particular cDNA may be accomplished by subcloning the cDNA into an appropriate expression vector and transfecting this vector into an appropriate expression host. The cloning vector used for the generation of the breast tissue cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription, as well as a number of unique restriction sites, including EcoRI, for cloning. The vector can be transfected into an appropriate host strain of E. coli.

Induction of the isolated bacterial strain with isopropylthiogalactoside (IPTG) using standard methods will produce a fusion protein that contains the first seven residues of beta-galactosidase, about 15 residues of linker and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include, but are not limited to, mammalian cells, such as Chinese Hamster Ovary (CHO) and human embryonic kidney (HEK) 293 cells, insect cells, such as Sf9 cells, yeast cells, such as *Saccharomyces cerevisiae* and bacteria, such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker, such as the neomycin phosphotransferase gene, to allow selection in transfected eukaryotic host cells. Vectors for use in eukaryotic expression hosts may require the addition of 3' poly A tail if the sequence of interest lacks poly A.

Additionally, the vector may contain promoters or enhancers that increase gene expression. Such promoters are host specific and include, but are not limited to, MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the Rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transfection of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

It is contemplated and within the scope of the present invention that the solid phase also can comprise any suitable porous material with sufficient porosity to allow access by detection antibodies and a suitable surface affinity to bind antigens. Microporous structures generally are preferred, but materials with a gel structure in the hydrated state may be used as well. Such useful solid supports include, but are not limited to, nitrocellulose and nylon. It is contemplated that such porous solid supports described herein preferably are in the form of sheets of thickness from about 0.01 to 0.5 mm, preferably about 0.1 mm. The pore size may vary within wide limits and preferably is from about 0.025 to 15 microns, especially from about 0.15 to 15 microns. The surface of such supports may be activated by chemical processes that cause covalent linkage of the antigen or antibody to the support. The irreversible binding of the antigen or antibody is obtained, however, in general, by adsorption on the porous material by poorly understood hydrophobic forces. Other suitable solid supports are known in the art.

EXAMPLES

Example 1

Isolation, Maintenance, and Labeling of Cell Lines

Paclitaxel-resistant CHO mutants used in this study and conditions for their growth in alpha modification of Minimum Essential Medium (α-MEM, GIBCO BRL, Gaithersburg, Md.) have been previously described (Cabral, F. (1983) *J. Cell Biol.* 97, 22–29; Cabral, F., Wible, L., Brenner, S., and Brinkley, B. R. (1983) *J. Cell Biol.* 97, 30–39; and Schibler, M., and Cabral, F. (1986) *J. Cell Biol.* 102, 1522–1531). Metabolic labeling was for 1 h in methionine-free MEM (ICN Biomedicals Inc., Costa Mesa, Calif.) containing 30 μCi/ml Tran $^{35}$S-label (1,000 Ci/mmol; ICN Biomedicals).

Example 2

Sequencing Mutant Beta-Tubulin

To analyze mutant alleles, the sequence of the wild-type CHO β1-tubulin gene (GenBank Accession number AF120325) was determined and then primers were used in the intron and 5' and 3' untranslated regions to amplify the coding sequences from mutant cell DNA. Sequencing was carried out using 2 different methods. In the first, amplified DNA was directionally cloned into M13mp18 or M13mp19, multiple individual plaques for each mutation were isolated, and phage DNA was sequenced by the dideoxy chain termination method (Sanger, F., Nicklen, S., and Coulson, A. R. (1977) *Proc. Natl. Acad. Sci. USA* 74, 5463–5467; and Sanger, F., Coulsen, A. R., Barrell, B. G., Smith, A. J. H., and Roe, B. (1980) *J. Mol. Biol.* 143, 161–178) using Sequenase (United States Biochemical Corp., Cleveland, Ohio). To enhance the ability to quickly scan for mutations, all the sequencing reactions for each dideoxy nucleotide were loaded in adjacent wells of the sequencing gel as previously described (Kobayashi, K., Jackson, M. J., Tick, D. B., O'Brien, W. E., and Beaudet, A. L. (1990) *J. Biol Chem* 265, 11361–7). Because CHO cells are diploid, mutations were easily identified as changes affecting half of the 6–8 plaques that were isolated from each PCR amplification. Polymerase (Pfu, Stratagene, La Jolla, Calif.) errors, on the other hand were rare and only affected 1 of the 6–8 plaques.

A second method involved direct sequencing of the PCR amplified DNA using an ABI Model 310 automated sequencer (Perkin-Elmer Corp., Foster City, Calif.). In this case, mutations were detected as coelution of 2 nucleotides from the capillary column when sequenced in both the forward and reverse directions. For both methods, mutations were confirmed by repeating the sequencing on freshly amplified DNA and by digesting the PCR amplified DNA whenever a restriction enzyme site was gained or lost.

Example 3

Construction of Plasmids

CHO Cβ1 cDNA (Boggs, B., and Cabral, F. (1987) *Mol. Cell. Biol.* 7, 2700–2707; and Boggs, B. A., Gonzalez-Garay, M. L., and Cabral, F. (1996) *DNA Sequence* 6, 171–174), modified to express a 9 amino acid hemagglutinin antigen (HA) tag at the C-terminus of β1-tubulin (Gonzalez-Garay, M. L., and Cabral, F. (1995) *Cell Motil. Cytoskeleton* 31, 259–272), was used for all transfections. To obtain regulated expression, pcDNA3 (Invitrogen, Carlsbad, Calif.) was modified to incorporate the features of the tetracycline regulated vector system described earlier (Gossen, M., and Bujard, H. (1992) *Proc. Natl. Acad. Sci. USA* 89, 5547–5551), and the new plasmid was named pTOPneo. A 1.5 kb Hind III/Not I fragment from plasmid BlskHAβ1 (Gonzalez-Garay, M. L., and Cabral, F.) containing the entire HAβ1-tubulin coding sequence was cloned into the unique Hind III/Not I sites of pTOPneo to create pTOPneo-HAβ1. This construct was used for all transfections and for site-directed mutagenesis to create mutant HAβ1-tubulins. All constructs were sequenced to confirm the mutations.

A second plasmid carrying the coding sequence of the tetracycline-regulated transactivator (tTA) was made by first replacing the neomycin resistance gene of pTOPneo with the puromycin resistance gene from the vector pPUR (Clontech Laboratories, Inc., Palo Alto, Calif.), to create pTOPpuro. The sequence for tTA was then added by cloning a 1 kb Eco RI/Bam HI fragment from the plasmid pUHD 15-1 (Gossen, M., and Bujard, H.) into pTOPpuro to create pTOPpuro-tTA.

Example 4

Transfection

Plasmid DNA was isolated using the QIAfilter Plasmid Maxi Kit (Qiagen Inc., Santa Clarita, Calif.) and transfected into CHO cell line tTApuro 6.6, obtained by transfecting wild-type CHO cells with pTOPpuro-tTA. Transfections were carried out using Lipofectamine (GIBCO BRL) and 1 μg of plasmid DNA according to the manufacturer's instructions except that 1 μg/ml tetracycline (Sigma Chemical Co., St. Louis, Mo.) was included at each step to inhibit expression of the cDNA until the time of analysis. Stable transfectants were isolated and maintained in medium containing 2 mg/ml G418 (GIBCO BRL) plus 1 μg/ml tetracycline, or 0.2 μg/ml paclitaxel with no tetracycline.

Example 5

Electrophoretic Procedures

For two-dimensional (2D) gel analysis, cells were lysed in buffer (20 mM Tris HCl, pH 6.8, 0.14 M NaCl, 2 mM EGTA, 1 mM $MgSO_4$, 0.5% Triton X-100) and centrifuged 5 min at 12,000 g. Proteins in the supernatant were precipitated by the addition of 5 volumes of acetone at 4û C, redissolved in solubilizing buffer (8 M urea, 5 mM Tris HCl, pH 6.8, 5 mM mercaptoethanol, 1% Triton X-100), and resolved by 2D gel electrophoresis as previously described (Cabral, F., and Schatz, G. (1979) *Methods Enzymol.* 56, 602–613).

For western blot analysis, cells were lysed with hot (100° C.) SDS dissociation buffer (Laemmli, U. K. (1970) *Nature* (Lond) 227, 680–685). Protein was precipitated with 5 volumes of acetone at 4° C. and centrifuged 5 min at 12,000 g. The pellet was redissolved in SDS dissociation buffer and run on a 7.5% polyacrylamide SDS minigel (Bio Rad Laboratories, Hercules, Calif.). Proteins were then electrophoretically transferred onto a nitrocellulose membrane (Towbin, H., Staehelin, T., and Gordon, J. (1979) *Proc. Natl. Acad. Sci. USA* 76, 4350–4354) and probed with a mixture of mouse monoclonal antibodies to β-tubulin (Tub 2.1, 1:2000 dilution, Sigma) and actin (C4, 1:5000 dilution, ICN). This was followed by incubation in peroxidase-conjugated goat antimouse IgG (1:2000 dilution, Cappel Laboratories, Cochranville, Pa.) and detection by chemiluminescence (Kirkegaard & Perry Laboratories, Inc., Gaithersburg, Md.) using the manufacturer's instructions.

Example 6

Immunofluorescence

Cells were grown on glass coverslips to approximately 70% of confluence and fixed in methanol (−20° C.) for at least 10 min as previously described (Gonzalez-Garay, M. L., and Cabral, F.). The primary antibody used for most experiments was mouse monoclonal 12CA5 (Boehringer Mannheim Corp., Indianapolis, Ind.), specific for the HA tag. This was followed by fluorescein conjugated goat antimouse IgG (Cappel). For double label experiments, mouse monoclonal 6-11B-1 (Sigma), specific for acetylated β-tubulin, was added together with rabbit antibody HA11 (Berkeley Antibody Co., Richmond, Calif.), specific for the HA tag. This was followed with a mixture of goat affinity purified and cross absorbed antibodies consisting of Oregon Green conjugated antirabbit IgG and Rhodamine Red-X-conjugated antimouse IgG (both from Molecular Probes, Inc., Eugene, Oreg.). Photographs were taken on TMAX 400 film (Eastman Kodak, Rochester, N.Y.) using an Optiphot

Example 7

Drug Resistance

The ability of β-tubulin mutations to confer paclitaxel resistance was evaluated in 2 ways. In the first, stably transfected cell lines expressing mutant HAβ1-tubulin were seeded at approximately 100 cells/well in replicate wells of a 24-well dish containing increasing concentrations of paclitaxel. The assay was carried out in duplicate with only one set containing 1 μg/ml tetracycline. After 6–7 d, the medium was removed and the resistant colonies were stained with a solution of 0.1% methylene blue as previously described (Cabral, F., Sobel, M. E., and Gottesman, M. M. (1980) *Cell* 20, 29–36). In a second assay, aliquots (~7×10$^4$ cells for selective, and ~100 cells for non-selective conditions) from total transfected cell populations were seeded into duplicate 6-well dishes containing normal medium (non-selective), 2 mg/ml G418, or 0.2 μg/ml paclitaxel, each with or without 1 μg/ml tetracycline. After the appearance of visible colonies (6–7 d), one duplicate dish was stained with methylene blue and colonies were counted. Cells in the second dish were trypsinized and replated onto glass coverslips for immunofluorescence observation.

Measurement of Tubulin Polymerization

The distribution of tubulin between the soluble and polymerized pools was measured using a previously published procedure (Minotti, A. M., Barlow, S. B., and Cabral, F. (1991) *J. Biol. Chem.* 266, 3987–3994). Briefly, cells were incubated for 2 generations (24 h) in [$^3$H]methionine to label the proteins to steady state, the cells were lysed with a microtubule stabilizing buffer, microtubules were separated from soluble tubulin by centrifugation, a constant amount of [$^{35}$S]methionine labeled CHO cell extract was added to each fraction, the proteins in each fraction were separated by 2D gel electrophoresis, and the $^3$H/$^{35}$S ratio for β-tubulin was determined by liquid scintillation counting of spots excised from the gels. This method gives very accurate and reproducible measurements of the fraction of tubulin in the assembled state (Minotti, A. M., et al.).

Results

Paclitaxel Resistant Cell Lines with Altered β-Tubulin

Our laboratory has isolated a large number of paclitaxel resistant CHO cells with diminished microtubule assembly (Cabral, F. (1983) *J. Cell Biol.* 97, 22–29; Schibler, M., and Cabral, F. (1986) *J. Cell Biol.* 102, 1522–1531; and Cabral, F., Abraham, I., and Gottesman, M. M. (1981) *Proc. Natl. Acad. Sci. USA* 78, 4388–4391). For the initial seqencing of these mutants, we focused on 6 cell lines that exhibited alterations in the two-dimensional (2D) gel migration of β-tubulin, but we also included 7 additional cell lines with no such alterations. Their 2D gel patterns are summarized in FIG. 1. The 7 mutants with an unaltered 2D gel pattern resembled wild-type cells in displaying a single spot for all the expressed forms of β-tubulin (FIG. 1A). The remaining 6 cell lines with an altered 2D gel pattern fell into 2 groups. Most displayed an additional β-tubulin spot with a more basic isoelectric point (arrowhead, FIG. 1B), but strain 11-3 had an additional β-tubulin spot with a more acidic isoelectric point (arrowhead, FIG. 1C). For the mutants with the gel pattern in FIG. 1B, the direction and magnitude of the shift from the wild-type position is consistent with a single charge difference as would be expected for the substitution of a basic for a neutral amino acid, or a neutral for an acidic amino acid. The direction of the shift in Tax 11-3, on the other hand, suggests the substitution of an acidic for a neutral amino acid, or a neutral for a basic amino acid. In all cases, the mutant product accounts for approximately ⅓ of the total β-tubulin produced (Sawada, T., and Cabral, F. (1989) *J. Biol. Chem.* 264, 3013–3020).

Drug Sensitivity of Paclitaxel Resistant Cells

Resistant cell lines were selected in one step to a single lethal dose of paclitaxel and are approximately 2-3 fold resistant to the drug. Some cell lines are additionally paclitaxel-dependent (Cabral, F.; Cabral, F., et al.; and Schibler, M., and Cabral, F.). This latter phenotype is easily recognized by a failure of the cells to divide when paclitaxel is omitted from the growth medium, and is characterized by a change in morphology to large multinucleated cells (Cabral, F., and Barlow, S. B.).

These properties are consistent with a model in which paclitaxel resistance mutations in tubulin destabilize microtubules (Cabral, F., Brady, R. C., and Schibler, M. J. (1986) *Ann. NY. Acad. Sci.* 466, 745–756; and Cabral, F., and Barlow, S. B. (1989) *FASEB J.* 3, 1593–1599). Direct measurements of the extent of tubulin assembly in mutant cell lines have supported this model (Minotti, A. M., Barlow, S. B., and Cabral, F.). Table I summarizes the extent of tubulin assembly in cell lines with β-tubulin mutations.

Particularly noteworthy is the observation that paclitaxel dependent mutants have a lower extent of microtubule assembly than wild-type or resistant cell lines, suggesting that paclitaxel dependent cells are not fundamentally different from resistant cells. Rather, they simply have mutations in tubulin that are more disruptive to microtubule assembly. Thus, paclitaxel resistance mutations produce a spectrum of alterations in microtubule assembly from minimally disruptive (resistant cells) to highly disruptive (dependent cells). It is anticipated that mutations that are even more disruptive would not be rescued by paclitaxel and therefore would not allow the cells to survive. Similarly, mutations that prevent assembly of altered tubulin would not be capable of conferring resistance to the drug and would be lost during the selection.

Leucine is Frequently Altered in Paclitaxel Resistant Cell Lines

To gain insight into the mutations that destabilize microtubule assembly, β1-tubulin from each of 13 mutant cell lines was sequenced. Four of the 7 mutants with a normal 2D gel pattern failed to exhibit an alteration in the β1-tubulin gene. This was an expected result because we have previously shown that mutations in both α- and β-tubulin confer paclitaxel resistance with equal frequency (Schibler, M., and Cabral, F.).

Mutations in the β1-tubulin gene from the remaining 3 mutants, plus the 6 mutants with an altered 2D gel pattern, are summarized in Table I. It was unexpected to find that 6 of the 9 mutations resulted in an amino acid substitution at leu215, and in 3 of these, leucine was replaced by histidine. It is unlikely that the 3 mutants with a histidine substitution represent sister clones because the cell lines came from independent selections, and the cells have distinctive morphologies. In addition to the his substitution at amino acid 215, only phe and arg substitutions were found. The remaining cell lines had L217R, L228F, and L228H substitutions. This clustering of mutations in a small region of β1-tubulin, all affecting leucine residues is remarkable and suggests a structural motif that may be critical for microtubule assembly.

Two of the cell lines exhibited more than a single base substitution in the β1-tubulin gene. Tax-18 has 2 C to T transitions within the same codon (CTC to TTT). Restriction enzyme digestion experiments indicated that both transitions in Tax-18 occurred in the same β1-tubulin allele. Tax 11-3 has a G38E substitution (GGA to GAA) in addition to the L228F substitution shown in Table I. The G38E substitution in Tax 11-3 explains the acidic shift observed for the mutant β1-tubulin on 2D gels (FIG. 1C), because the L228F substitution in this mutant is expected to be electrophoretically silent. Transfection experiments (described later) indicate that the G38E mutation does not contribute to paclitaxel resistance, a conclusion that is consistent with the observation that 48 of 48 revertants of this strain retained the G38E mutation as evidenced by retention of the acidic shift in the position of the mutant β-1-tubulin on 2D gels (Schibler, M., and Cabral, F.).

Stable Transfection of Mutant HA Beta 1-Tubulin cDNA

Although the amino acid substitutions we have uncovered in paclitaxel resistant mutants predict amino acid changes that are consistent with the mobilities of the altered β1-tubulins on 2D gels (e.g., see FIG. 3), it is possible that other alterations in these cell lines may also contribute to the resistance phenotype. For example, Tax 2-4 (Table I) has a more extreme phenotype than Tax 1-4 or Tax 4-9, even though it has the same L215H mutation. Based on its very low reversion frequency (Schibler, M., and Cabral, F.), it has long been suspected that Tax 2-4 may have a second mutation; but we have not sequenced all of the remaining tubulin genes to confirm this suspicion. To avoid the ambiguities inherent in trying to assign phenotypes to observed biochemical or genetic changes in the mutant cell lines, the strategy of recreating the mutations in a cloned cDNA and directly demonstrating that transfection of that cDNA is sufficient to confer paclitaxel resistance was adopted. To accomplish this, a chimeric CHO β-1-tubulin cDNA encoding a 9 amino acid hemagglutinin antigen (HA) epitope tag at the C-terminus of the polypeptide (Gonzalez-Garay, M. L., and Cabral, F.), was modified by site directed mutagenesis to introduce the L215H, L217R, and L228F substitutions. We circumvented the possibility that overexpression of these mutant genes might be toxic to transfected cells by inserting the altered tubulin cDNAs into a pTOPneo vector that places the gene to be expressed under the control of a minimum CMV promoter whose activity requires the binding of a tetracycline regulated transactivator to an upstream bacterial tetO sequence (Gossen, M., and Bujard, H.). Each of the mutant cDNAs, as well as an unmodified HAβ1-tubulin, was transfected into a CHO strain (tTA/puro 6.6) that was isolated in this laboratory and produces the tetracycline regulated transactivator in the absence, but not the presence, of tetracycline.

Stable G418-resistant cell lines from each of the transfections were isolated and screened for production of HA tagged β-tubulin by immunofluorescence. Approximately half of the cell lines for each transfection proved to be positive, and some examples of these are shown in FIG. 4. For each clone, >95% of the cells in the population stained positive for HAβ1-tubulin production. To obtain a more quantitative estimate for the fraction of total β-tubulin represented by the HAβ1-tubulin in each cell line, western blot analysis with an antibody that recognizes both forms of β-tubulin was carried out (FIG. 5). The HAβ1 transfectant exhibited a very high level of HAβ-tubulin production, resulting in a cell line in which the majority of the endogenous β-tubulin is replaced by the epitope tagged tubulin at steady state. The HAβ1$_{L217R}$ and HAβ1$_{L228F}$ transfectants also had high production of HAβ-tubulin, but the endogenous β-tubulin remained a significant component. The lowest level of HAP-tubulin was found in the HAβ1$_{L215H}$ transfectant, where it accounted for only a small fraction of the total β-tubulin in the cell. In all 4 cases, production of HA tagged tubulin was undetectable by immunofluorescence or western blot analysis when the cells were grown in tetracycline.

Expression of Mutant HA Beta 1-Tubulin Destabilizes Cellular Microtubules

Although all transfectants producing wild-type HAβ1-tubulin grew well in the absence of tetracycline, transfectants producing moderate to high levels of mutant HAβ1-tubulin grew poorly. These latter cells frequently exhibited extensive multinucleation during interphase, and there was a clear increase in the number of mitotic cells indicating a block in mitosis. These observations are consistent with the reduced tubulin assembly measured in the mutants listed in Table I. To further demonstrate that incorporation of mutant HAβ1-tubulin destabilizes cellular microtubules, an HAβ1$_{L215H}$ transfected cell population was selected in G418 and double stained with antibodies to the HA tag and to acetylated β-tubulin. Work in other laboratories has demonstrated that acetylated tubulin is found in the most stable and least dynamic microtubules in the cell (Piperno, G., LeDizet, M., and Chang, X. (1987) *J. Cell Biol.* 104, 289–302; and Schulze, E., and Kirschner, M. (1987) *J. Cell Biol.* 104, 277–288). It was predicted that incorporation of mutant HAβ1-tubulin would cause microtubule destabilization and lead to reduced β-tubulin acetylation. The G418-selected population from cells transfected with HAβ1$_{L215H}$ was approximately 50% positive for expression, a value we have noted in previous transfection experiments (Gonzalez-Garay, M. L., and Cabral, F. (1995) *Cell Motil. Cytoskeleton* 31, 259–272; Barlow, S. B., Gonzalez-Garay, M. L., West, R. R., Olmsted, J. B., and Cabral, F. (1994) *J. Cell Biol.* 126, 1017–1029; and Gonzalez-Garay, M. L., and Cabral, F. (1996) *J. Cell Biol.* 135, 1525–1534). FIG. 6A shows two adjacent cells in this population, one of which was positive (small arrow), and the other of which was negative (large arrow), for mutant HAβ1-tubulin production. When the same cells were viewed for acetylated β-tubulin staining (FIG. 6B), a reciprocal relationship was evident. The cell that expressed mutant HAβ1-tubulin had little acetylation of β-tubulin, but the cell that did not express mutant tubulin had abundant β-tubulin acetylation. This result supports the notion that incorporation of mutant HAβ1-tubulin produces less stable microtubules.

Expression of Mutant HAβ-1-Tubulin is Sufficient to Confer Paclitaxel Resistance Measurement of drug resistance using a standard cloning efficiency assay was complicated by the observation that clones producing moderate to high levels of mutant HAβ1-tubulin grew poorly and produced many multinucleated cells. This problem was circumvented in 2 different ways. The first came from an observation that among the multinucleated cells, there were some cells that still looked normal. This suggested that some of the cells in the population might be expressing lower amounts of the mutant tubulin and might be able to survive when cultured without tetracycline. To select these cells, clones transfected with mutant HAβ1-tubulin were incubated in tetracycline-free medium containing a concentration of paclitaxel (0.2 μg/ml) that is lethal to wild-type cells. Multiple individual colonies were selected and tested for their dose response to paclitaxel; representative results are shown in FIG. 7. Although the logic of demonstrating paclitaxel resistance in a paclitaxel selected cell line might seem circular, we were able to make use of the fact that mutant HAβ1-tubulin is not expressed when tetracycline is present in the growth medium. Thus HAβ1, HAβ1L215H, HAβ1$_{L217R}$, and HAβ1$_{L228F}$ expressing cells were all tested for paclitaxel sensitivity in the presence or absence of tetracycline. It was found that the HAβ1 transfected cells had the same sensitivity to paclitaxel regardless of whether the HAβ1 tubulin is expressed (no tetracycline) or not expressed (with tetracycline). The cells transfected with mutant HAβ1-tubulin also had wild-type paclitaxel sensitivity when grown with tetracycline, but exhibited clear resistance to the drug when mutant tubulin production was induced by growing the cells without tetracycline.

To rule out the possibility that we may have biased the results by examining specific clones of mutant HAβ1-tubulin expressing cells, we also tested the relative abilities of G418 and paclitaxel to select mutant HAβ1-tubulin positive cells from the total transfected cell populations. We reasoned that paclitaxel should be a powerful agent for selection of mutant HAβ1-tubulin expressing cells if, and only if, the mutant tubulin is capable of conferring resistance to the drug. To test this prediction, aliquots from an HAβ1$_{L215H}$ transfected cell population were grown under 6 different conditions: normal medium, medium containing 2 mg/ml G418, and medium containing 0.2 µg/ml paclitaxel, each in the presence or absence of 1 µg/ml tetracycline. Using the number of colonies obtained under nonselective conditions (normal medium containing tetracycline) as a control, the relative cloning efficiencies under the various selective conditions are summarized in Table II.

TABLE II

Cloning Efficiencies of HAβ1$_{L215H}$ Transfected Cells under Various Selective Conditions

|  | +Tetracycline | −Tetracycline |
| --- | --- | --- |
| αMEM | 1 | 0.98 |
| G418 | $1.3 \times 10^{-3}$ (100) | $7.9 \times 10^{-4}$ (60) |
| Paclitaxel | $1.4 \times 10^{-5}$ (1) | $2.3 \times 10^{-4}$ (18) |

In Table II, CHO cell line tTApuro 6.6 was transfected with HAβ1$_{L215H}$ cDNA. At 24 h post-transfection, the cells were trypsinized and replated in normal medium (αMEM), medium containing 2 mg/ml G418, or medium containing 0.2 µg/ml paclitaxel, all either in the presence or absence of 1 µg/ml tetracycline. After 6–10 d (when visible colonies were seen) the cells were stained with methylene blue and the surviving colonies were counted. The cloning efficiency was calculated as the number of colonies obtained under selective conditions (G418 or paclitaxel) divided by the number of colonies obtained under nonselective conditions (αMEM+tetracycline). Numbers in parentheses are the number of colonies obtained relative to G418+tetracycline which was arbitrarily set at 100.

The highest cloning efficiency under selective conditions was obtained with G418 in the presence of tetracycline. This was expected because under these conditions, HAβ1$_{L215H}$ cDNA is not expressed and therefore, transfected cells should be capable of expressing the neomycin resistance gene without suffering negative consequences of HAβ1$_{L215H}$-tubulin production. The efficiency using G418 under inducing conditions (no tetracycline) was about 40% lower, consistent with the expectation that high expression of HAβ1$_{L215H}$ is deleterious to cell growth. To demonstrate that this is the correct explanation, cells selected under both conditions were compared by immunofluorescence using antibodies to the HA tag. The population selected in G418 under non-inducing conditions but assayed following induction, contained approximately 50% HA-positive cells (FIG. 8A). In stark contrast, cells selected in G418 under inducing conditions were fewer than 10% HA-positive and exhibited weaker fluorescence, indicating that only the cells with lower levels of expression were able to survive (FIG. 6B).

Selection in paclitaxel under inducing conditions was 5 times less efficient than in G418 with tetracycline (Table II). This can be explained by the loss of cells that produce too little HAβ1$_{L215H}$-tubulin to confer resistance or produce too much HAβ1$_{L215H}$-tubulin to survive. In contrast to the G418 selected cells, virtually all the cells selected in paclitaxel expressed HAβ1$_{L215H}$-tubulin (FIG. 8D). Thus, paclitaxel is a more stringent agent for selecting mutant HAβ1-tubulin expressing cells than is G418, and this strongly argues that HAβ1$_{L215H}$ tubulin confers resistance to the drug. Consistent with this interpretation, cells selected with paclitaxel under non-inducing conditions formed 18-fold fewer colonies. Cells selected under these conditions grew very poorly and needed to be cultured an additional week in order to obtain enough cells for analysis. The resultant cells (FIG. 8C) were <5% positive for HAβ1$_{L215H}$-tubulin expression and exhibited weaker fluorescence than the cells selected under inducing conditions. Unlike the cells selected for paclitaxel resistance under inducing conditions, which repressed HAβ1$_{L215H}$ tubulin expression upon tetracycline addition, the HA-positive cells selected under non-inducing conditions remained positive regardless of whether tetracycline was present or absent (data not shown). These results indicated that the few cells selected with paclitaxel in the presence of tetracycline consisted of non-transfected cells with borderline paclitaxel resistance (and severe growth problems) and transfected cells with low, unregulated HAβ1$_{L215H}$-tubulin production.

The preceding data gave us confidence that direct selection of paclitaxel resistant transfected cells, followed by analysis of transfected gene expression in the selected population, can serve as a rapid and reliable method for testing the ability of various mutations to confer drug resistance. Indeed, when the procedure was repeated three times with HAβ1, or with HAβ1$_{G38E}$ (a random mutation in Tax 11-3) cDNAs, no paclitaxel resistant cells were obtained despite the selection of thousands of G418 resistant colonies. In contrast, HAβ1$_{L217R}$ and HAβ1$_{L228F}$ cDNAs behaved like the HAβ1$_{L215H}$ cDNA and gave many paclitaxel resistant colonies, all of which were positive for expression of the mutant gene. We conclude that HAβ1$_{L215H}$, HAβ1$_{L217R}$, and HAβ1$_{L228F}$ mutations are sufficient to confer paclitaxel resistance in CHO cells.

Discussion

The nucleotide positions that can be mutated to produce the most common L215, L217 and L228 mutations include: 643 or 644 (L215), 649 or 650 (L217), and 682 or 683 (L228). Numbering starts at the beginning of the coding sequence. Note that the third nucleotide of the codon for leucine is degenerate and therefore mutations at the third position (645, 651 and 684) will not lead to an amino acid substitution.

The tight distribution of mutations producing paclitaxel resistance was surprising and unexpected. All 9 amino acid substitutions changed one of 3 leucine residues that were within 14 amino acids of one another. The inventors have created additional mutations in the H6/H7 loop of beta tubulin (that contains L215 and L217) and find that the following also are capable of conferring paclitaxel resistance: T214A, L215A, L215E, L215M, L215P, K216A, L217A and L228A. Possible reasons these mutations were not found in a direct selection for paclitaxel resistant cells include:

a) they cannot be created by a single base substitution,
b) they impart a growth disadvantage to the cell, or
c) the level of expression needed for resistance is inconsistent with the fixed stoichiometry of tubulin in the cell.

Regarding the latter point, thus far, CHO cells have all tubulin mutations in one of the two class I beta tubulin genes that are expressed. A mutation in one allele would result in a fixed level of mutant subunit accounting for about ⅓ of the total tubulin. Some mutations might require higher levels of expression to produce reisistance while others might be too toxic at that level. This indicates that other mutations in the H6/H7 loop of beta tubulin, especially the leucine 214, 215, 216, 217 and 228, are important to resistance. These mutations can confer resistance alone or in combinations with each other.

The focus of the prior art is on another region (the "M" loop representing the S7-H9 loop) as the main region involved in microtubule assembly and where mutations would be expected to effect resistance. No special significance was ascribed to the H6/H7 loop where the instant mutations have been found. Thus, the significance of the H6/H7 loop in microtubule assembly and paclitaxel resistance could not have been predicted merely from disclosures in the prior art. The inventors have discovered that the mutations in the H6H7 region affect resistance to paclitaxel-like drugs.

The specific mutants are cross-resistant to any drug that stabilizes microtubules. A number of pacliltaxel derivatives are being tested for utility in cancer and one of them, taxotere, is well along in clinical trials. Furthermore, other novel compounds such as the epothilones and discodermolide are being developed for cancer therapy. Because the present mutants are cross resistant to all compounds that stabilize microtubules, any drug which works to stabilize microtubules would be ineffective against tumors having these mutations.

The inventors have begun to isolate human cells resistant to paclitaxel in a KB3 cervical carcinoma cell line. Preliminary evidence indicates that the same mechanism of resistance that was described in CHO cells is the predominant mechanism in human cells; i.e., the mutant cells are resistant to paclitaxel, but are hypersensitive to vinblastine and other drugs that cause microtubule disassembly.

The high incidence of mutations in one region of the β-tubulin gene in paclitaxel resistant mutants is not likely to be the result of a mutational "hot spot" for the following reasons: 1) A sequence comparison between β1-tubulin from our laboratory strain of CHO cells and a β1-tubulin cDNA we isolated from a CHO library that was produced in a different laboratory, revealed 77 randomly dispersed nucleotide differences within the coding region. None of the nucleotide changes, including a change in codon 228 from CTC to CTG, affected the amino acid sequence. 2) Tax 11-3 has a second mutation (G38D) at a distant location that does not contribute to the paclitaxel resistance phenotype. 3) One mutation that confers Colcemid resistance and 5 that prevent β-tubulin assembly into microtubules are distant from the 215–228 codons.

An alignment of β-tubulin sequences in GenBank indicates that the 3 leucine residues are invariant with the exception of an ileu for leu substitution at amino acid 217 in Schizosaccharyomyces pombe. Furthermore, the conservation of leucines at 215 and 228 extends to α- and γ-tubulin (Erickson, H. P. (1998) *Trends in Cell Biol.* 8, 133–137). The results suggest that the 3 residues play an important role in microtubule assembly and in the mechanism of action of paclitaxel.

Because all 3 mutated leucines in CHO β1-tubulin use a CTC codon, 6 possible amino acid substitutions are permitted by single base mutations. Of these, only 3 (his, phe, arg) were actually recovered; furthermore, they were recovered multiple times. Although the number of mutants analyzed is limited, this result could imply that the remaining amino acid substitutions (pro, val, ileu) produce mutant tubulin that is 1) assembly competent but minimally disruptive to microtubule structure and therefore unable to confer paclitaxel resistance, 2) assembly competent but too disruptive to microtubule structure for the cells to survive selection, or 3) assembly incompetent and therefore unable to confer paclitaxel resistance. In this regard, it should be noted that substitutions of hydrophobic (phe) or charged (arg, his) amino acids can confer resistance. This suggests that it may be the size of the substitution rather than its charge or polarity that destabilizes the microtubules. By this criterion, val and ileu may not perturb the structure sufficiently to confer resistance, but pro might perterb microtubule structure so much that it is toxic to the cells. In support of this hypothesis, direct transfection of cDNAs failed to produce pclitaxel resistant cells. In contrast, transfection of a cDNA encoding the L215P variant was able to produce cells that were paclitaxel-resistant, but cells with only low levels of expression were recovered. This suggests that higher level of expression may be toxic to cells and this might explain the failure to isolate L215P mutants in a direct selection of CHO cells for resistance to paclitaxel.

The recent publication of the electron crystal structure of tubulin (Nogales, E., Wolf, S. G., and Downing, K. H. (1998) *Nature* 391, 199–203) indicates that mutations in codons 215 and 217 are in a loop connecting helices H6 and H7, while the 228 mutation falls within the H7 helix itself. The H6/H7 loop is close to paclitaxel and part of the loop (i.e. residues 217–231) has been photocrosslinked to 2-(m-azidobenzoyl) paclitaxel (Rao, S., Orr, G. A., Chaudhary, A. G., Kingston, D. G., and Horwitz, S. B. (1995) *J. Biol. Chem.* 270, 20235–8). These data predict that the H6/H7 loop might be involved in binding paclitaxel, but the instant mutants clearly do not have altered paclitaxel binding. Instead they are resistant because the mutations in tubulin produce less stable microtubules that can more easily withstand the stabilizing effects of paclitaxel—a mechanism that the inventors are the first to describe. Consistent with the idea that the H6/H7 loop is not involved with paclitaxel binding, the crystal structure predicts that residue L275 forms the main interaction with the taxane ring (Nogales, E., et al.) and genetic studies implicate residues F270 and A364 as part of the paclitaxel binding site. (Giannakakou, P., Sackett, et al.).

The mutant properties themselves also argue that altered paclitaxel binding is not responsible for drug resistance in our mutants (Cabral, F., Brady, R. C.). For example, β-tubulin is reported to contain the paclitaxel binding site, yet mutations conferring paclitaxel resistance occur with equal frequency in both α- and β-tubulin and both groups of mutants exhibit similar properties (Schibler, M., and Cabral, F.). Many paclitaxel resistant mutants require the drug for cell division and therefore must clearly retain the ability to bind the drug. Also, paclitaxel resistant mutants frequently exhibit increased sensitivity to drugs such as colchicine and vinblastine that bind to distinctly different sites. Instead of altered drug binding, we favor a mechanism in which paclitaxel binding alters the conformation or position of the loop connecting H6 and H7 of β-tubulin in such a way as to facilitate and stabilize subunit—subunit interactions important in the formation of microtubules.

The position of the H6/H7 loop in crystal structure (Nogales, E., Whittaker, M., Milligan, R. A., and Downing, K. H. (1999) *Cell* 96, 79–88) is consistent with a role in longitutinal or lateral interactions in microtubule assembly. The focus of the crystallography papers, however, is on another region (the "M" loop representing the S7-H9 loop) as the main region involved in microtubule assembly. No special significance was ascribed to the H6/H7 loop in microtubule assembly and paclitaxel could not have predicted from the structure. The mutations we have identified in leucines 215, 217, and 228 could potentially counteract the effects of paclitaxel by weakening those same interactions directly, or by preventing or mitigating the putative conformational change resulting from drug binding. Because the mutations appear to destabilize microtubule assembly in the absence of any drug (Table I and Minotti, A. M., Barlow, S. B., and Cabral, F. (1991) *J. Biol. Chem.* 266, 3987–3994), a direct effect on subunit—subunit interactions appears the more likely possibility.

Because other mechanisms have been proposed to account for paclitaxel-resistance in various cell lines, it is worth commenting on possible reasons that assembly mutations occur at such high frequency in CHO cells. Although we have previously demonstrated that CHO cells selected for resistance to colchicine and to vinblastine have a high incidence of the MDR phenotype (Schibler, M. J., Barlow, S. B., and Cabral, F. (1989) *FASEB J.* 3, 163–168), selections for paclitaxel resistance yield primarily tubulin assembly mutations (Schibler, M., and Cabral, F. (1986)). This difference in frequency could result from different affinities of the drugs for the P-glycoprotein involved in pumping drugs out of mdr cells, but in our view is more likely to result from the fact that mutations in tubulin that destabilize microtubule assembly are relatively common. On the other hand, mutations in tubulin that enhance microtubule assembly, as would be needed for resistance to colchicine or vinblastine, should be relatively rare.

The preceding argument could explain why tubulin mutations are more common in paclitaxel-resistant compared to colchicine- or vinblastine-resistant cells, but does not explain why others have reported mdr as the major mechanism of resistance to paclitaxel (Casazza, A. M., and Fairchild, C. R. (1996) *Cancer Treatment &Research* 87, 149–71). To understand the cause for this difference, it is important to examine the means by which the resistant cells were obtained. In most other studies, multiple step selections were carried out, yielding cells with very high levels of resistance to paclitaxel. Such procedures bias the types of mutations that are ultimately recovered. Mutations in, or amplification of, P-glycoprotein are not detrimental to the growth of cells in culture and thus are retained when selecting for high levels of resistance. In contrast, mutations in tubulin are very likely to affect cell survival if they are too severe and thus would be lost (or at least not predominate) in any selection to high levels of resistance. Since we used single-step selections yielding cells with only 2-3 fold resistance to paclitaxel, there was less bias against the isolation of tubulin mutations compared to multistep procedures. In support of this explanation, selection of human lung carcinoma cells for paclitaxel resistance in a single step also yielded a cell line with altered tubulin rather than mdr (Ohta, S., Nishio, K., Kubota, N., Ohmori, T., Funayama, Y., Ohira, T., Nakajima, H., Adachi, M., and Saijo, N. (1994) *Jpn. J. Cancer Res.* 85, 290–297).

In addition to cells with tubulin assembly mutations or altered P-glycoprotein mediated mdr, human ovarian cell lines with mutations in β-tubulin that may affect paclitaxel binding have recently been described (Giannakakou, P., et al.). The inventors have not identified similar mutants in our single step selections and have long argued that such mutations should not occur at high frequency in mammalian cells because drug binding mutations are recessive and mammalian cells are diploid for expression of multiple tubulin genes (Sullivan, K. F. (1988) *Ann. Rev. Cell Biol.* 4, 687–716). Indeed, the paclitaxel resistant human ovarian cells were gradually selected to higher levels of resistance than can normally be obtained in a simple one-step procedure and were 24-fold more resistant than the unselected cells. Furthermore, the authors found that both mutants were functionally hemizygous; i.e., only the mutant, but not the wild-type, allele was expressed. Since other β-tubulin isotypes are expressed at very low levels in this cell line, the mutant cells expressed the mutant polypeptide as the predominant β-tubulin species. Thus, at least 2 changes were required to obtain the drug binding phenotype, confirming that such changes should only occur at relatively low frequency.

Finally, a number of laboratories have reported changes in β-tubulin isotype expression that correlate with the acquisition of paclitaxel resistance in various cell lines (Haber, M., Burkhart, C. A., Regl, D. L., Madafiglio, J., Norris, M. D., and Horwitz, S. B. (1995) *J. Biol. Chem.* 270, 31269–75; Jaffrezou, J. P., Dumontet, C., Derry, W. B., Duran, G., Chen, G., Tsuchiya, E., Wilson, L., Jordan, M. A., and Sikic, B. I. (1995) *Oncology Res.* 7, 517–27; Kavallaris, M., Kuo, D. Y. S., Burkhart, C. A., Regl, D. L., Norris, M. D., Haber, M., and Horwitz, S. B. (1997) *J. Clin. Invest.* 100, 1282–93; and Ranganathan, S., Dexter, D. W., Benetatos, C. A., and Hudes, G. R. (1998) *Biochim. Biophys. Acta* 1395, 237–245). Again, however, these cells were selected in multiple step procedures that may have introduced bias into the kinds of mutants that survived selection. Furthermore, it has not yet been convincingly demonstrated that the altered β-tubulin isotype expression reported in these cell lines is responsible for the drug resistance phenotype. As previously pointed out (Giannakakou, P., et al.), it is possible that the multiple-step procedures used in those studies enriched for cells that amplified a minor isotype carrying a tubulin mutation that is actually responsible for conferring the resistance. In support of this possibility, Overexpression of class I, II, and Ivb isotypes of beta—tubulin were shown to be insufficient to produce paclitaxel resistance in CHO cells (Blade, K., Menick, D. R., and Cabral F. (1999) *J. Cell Sci.*, 112, 2213–2221.

In contrast, it is clear that the mutations described herein are capable, by themselves, of conferring paclitaxel resistance: transfection of an HA-tagged β1-tubulin cDNA containing mutations at any of the three leucine residues was sufficient to confer resistance in a wild-type CHO cell line. On the other hand, expression of HA-tagged β-tubulin cDNA lacking any mutations, or containing an irrelevant mutation (G38D), had no effect on paclitaxel resistance. In fact, the following mutations have been tested and do not produce appreciable paclitaxel resistance when produced at levels up to 50% of total beta tubulin in the cell:

G38D: This is an irrelevant second mutation found in one of our paclitaxel resistant mutants. See JBC 274:23875–23882, 1999.

D45Y: A mutation found in one of our colcemid resistant mutants.

L215V and L215I: Two mutations created by site directed mutagenesis that fail to produce paclitaxel resistance when transfected back into wild-type CHO cells. The valine and isoleucine substitutions at his position do not appear to disrupt the structure of tubulin sufficiently to produce resistance.

L215P: This mutation does produce resistance but only when expressed at very low levels. Higher levels of expression are toxic and the cells do not survive. In contrast to the original mutants in which altered beta-tubulin accounts for approximately 35% of the total, transfected cells are more variable in their production of mutant tubulin and this leads to greater heterogenity in their response to paclitaxel. Cells in the L215P transfected population that stained less brightly with antibodies to the HA tag grew very well in the absence of paclitaxel, but cells that stained very brighly became multi-nucleated when paclitaxel was removed from the growth medium.

These observations are consistent with a model proposed earlier suggesting that tubulin mutations causing paclitaxel resistance produce varying destabilization of microtubule assembly, with only the most severe mutations causing paclitaxel dependence (Cabral, F., and Barlow, S. B.). The inventors further demonstrate that the level of expression of mutant β-tubulin can cause varying destabilization of microtubule assembly with higher expression resulting in paclitaxel dependence. This may explain why the L217R mutation, which is not associated with paclitaxel dependence in the original mutant, is able to impart a paclitaxel-dependent phenotype on a subpopulation of the transfected cells. Similar observations have previously been reported for the creation of a Colcemid-dependent cell line by transfection of DNA from Colcemid-resistant cells into wild-type CHO cells (Whitfield, C., Abraham, I., Ascherman, D., and Gottesman, M. M. (1986) *Mol. Cell. Biol.* 6, 1422–1429). This line of reasoning suggests that the severity of a mutation, and its ultimate effects on microtubule stability and paclitaxel resistance, depends not only on the nature of the mutation, but also on the level of expression of the mutant allele in a given cell line.

The present analysis involves mutations in β-tubulin; and it is known from two-dimensional gel analysis that mutations in alpha-tubulin are equally prevalent in paclitaxel resistant cells (Schibler, M., and Cabral, F.). It is may be speculated that the alpha-tubulin mutations able to confer paclitaxel resistance will also cluster in a few residues. Further, the mutations found in beta tubulin may produce resistance if introduced into alpha tubulin because the region around the mutations is highly conserved in both subunits.

The specific mutants are cross resistant to any drug that stabilizes microtubules. A number of paclitaxel derivatives are being tested for utility in cancer and one of them, taxotere, is well along in clinical trials. Furthermore, other novel compounds such as the epothilones and discodermolide are being developed for cancer therapy. Because the present mutants are cross resistant to all compounds that stabilize microtubules, all drugs that act by stabilizing microtubules could be ineffective against these tumor cells.

The inventors have begun to isolate human cells resistant to paclitaxel in a KB3 cervical carcinoma cell line. Preliminary evidence indicates that the same mechanism of resistance that we described in CHO cells is the predominant mechanism in human cells, i.e., the mutant cells are resistant to paclitaxel but are hypersensitive to vinblastine and other drugs that cause microtubule disassembly.

The mutant sequences and identified wild-type sequence can also be used for the development of antibodies, peptides or drugs that affect microtubule assembly and/or response to antimiotic drugs.

Although the invention has been disclosed with reference to its preferred embodiments, from reading this description those of skill in the art may appreciate changes and modification that may be made which do not depart from the scope and spirit of the invention as described above and claimed hereafter.

SEQUENCE LISTING

```
<160> NUMBER OF SEQ ID NOS: 26

<210> SEQ ID NO 1
<211> LENGTH: 15
<212> TYPE: DNA
<213> ORGANISM: Cricetulus griseus
<220> FEATURE:
<221> NAME/KEY: misc_feature
<222> LOCATION: (1)..(15)
<223> OTHER INFORMATION: Wild-type 214 to 218 sequence

<400> SEQUENCE: 1
actctcaagc tcacc                                                      15

<210> SEQ ID NO 2
<211> LENGTH: 15
<212> TYPE: DNA
<213> ORGANISM: Cricetulus griseus
<220> FEATURE:
<221> NAME/KEY: mutation
<222> LOCATION: (4)..(6)
<223> OTHER INFORMATION: 215 Leu to His mutation
```

```
<400> SEQUENCE: 2
actcacaagc tcacc                                              15

<210> SEQ ID NO 3
<211> LENGTH: 15
<212> TYPE: DNA
<213> ORGANISM: Cricetulus griseus
<220> FEATURE:
<221> NAME/KEY: mutation
<222> LOCATION: (4)..(6)
<223> OTHER INFORMATION: 215 Leu to Arg mutation

<400> SEQUENCE: 3
actcgcaagc tcacc                                              15

<210> SEQ ID NO 4
<211> LENGTH: 15
<212> TYPE: DNA
<213> ORGANISM: Cricetulus griseus
<220> FEATURE:
<221> NAME/KEY: mutation
<222> LOCATION: (4)..(6)
<223> OTHER INFORMATION: 215 Leu to Phe mutation - TTT codon

<400> SEQUENCE: 4
acttttaagc tcacc                                              15

<210> SEQ ID NO 5
<211> LENGTH: 15
<212> TYPE: DNA
<213> ORGANISM: Cricetulus griseus
<220> FEATURE:
<221> NAME/KEY: mutation
<222> LOCATION: (4)..(6)
<223> OTHER INFORMATION: 215 Leu to Phe mutation - TTC codon

<400> SEQUENCE: 5
actttcaagc tcacc                                              15

<210> SEQ ID NO 6
<211> LENGTH: 15
<212> TYPE: DNA
<213> ORGANISM: Cricetulus griseus
<220> FEATURE:
<221> NAME/KEY: mutation
<222> LOCATION: (10)..(12)
<223> OTHER INFORMATION: 217 Leu to Arg mutation

<400> SEQUENCE: 6
actctcaagc gcacc                                              15

<210> SEQ ID NO 7
<211> LENGTH: 15
<212> TYPE: DNA
<213> ORGANISM: Cricetulus griseus
<220> FEATURE:
<221> NAME/KEY: misc_feature
<222> LOCATION: (1)..(15)
<223> OTHER INFORMATION: wild-type from positions 226-230

<400> SEQUENCE: 7
aaccacctcg tctcg                                              15

<210> SEQ ID NO 8
<211> LENGTH: 15
<212> TYPE: DNA
```

```
<213> ORGANISM: Cricetulus griseus
<220> FEATURE:
<221> NAME/KEY: mutation
<222> LOCATION: (7)..(9)
<223> OTHER INFORMATION: Leu 228 to Phe mutation

<400> SEQUENCE: 8
aaccacttcg tctcg                                                        15

<210> SEQ ID NO 9
<211> LENGTH: 15
<212> TYPE: DNA
<213> ORGANISM: Cricetulus griseus
<220> FEATURE:
<221> NAME/KEY: mutation
<222> LOCATION: (7)..(9)
<223> OTHER INFORMATION: Leu 228 to His mutation

<400> SEQUENCE: 9
aaccaccacg tctcg                                                        15

<210> SEQ ID NO 10
<211> LENGTH: 21
<212> TYPE: DNA
<213> ORGANISM: Cricetulus griseus
<220> FEATURE:
<221> NAME/KEY: primer_bind
<222> LOCATION: (1)..(21)
<223> OTHER INFORMATION: wild-type beta tubulin primer

<400> SEQUENCE: 10
ctccgtaggt gggcgtggtg a                                                 21

<210> SEQ ID NO 11
<211> LENGTH: 21
<212> TYPE: DNA
<213> ORGANISM: Cricetulus griseus
<220> FEATURE:
<221> NAME/KEY: primer_bind
<222> LOCATION: (1)..(21)
<223> OTHER INFORMATION: mutant beta tubulin primer

<400> SEQUENCE: 11
ctccgtaggt gggcgtggcg c                                                 21

<210> SEQ ID NO 12
<211> LENGTH: 444
<212> TYPE: PRT
<213> ORGANISM: Cricetulus griseus
<220> FEATURE:
<221> NAME/KEY: MISC_FEATURE
<222> LOCATION: (1)..(444)
<223> OTHER INFORMATION: wild type beta-tubulin

<400> SEQUENCE: 12
```

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

-continued

```
Phe Gly Gln Ile Phe Arg Pro Asp Asn Phe Val Phe Gln Ser Gly
                 85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Glu Ala
        435                 440
```

<210> SEQ ID NO 13
<211> LENGTH: 444
<212> TYPE: PRT
<213> ORGANISM: Cricetulus griseus
<220> FEATURE:
<221> NAME/KEY: VARIANT
<222> LOCATION: (214)..(214)
<223> OTHER INFORMATION: Thr to Ala beta-tubulin substitution variant

<400> SEQUENCE: 13

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Ala Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415
```

```
Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
        435                 440

<210> SEQ ID NO 14
<211> LENGTH: 444
<212> TYPE: PRT
<213> ORGANISM: Cricetulus griseus
<220> FEATURE:
<221> NAME/KEY: VARIANT
<222> LOCATION: (215)..(215)
<223> OTHER INFORMATION: Leu to Ala beta-tubulin substitutional variant.

<400> SEQUENCE: 14

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Ala Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320
```

```
Met Ser Met Lys Glu Val Asp Glu Gln Met Leu Asn Val Gln Asn Lys
            325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
            355                 360                 365

Gly Asn Ser Thr Ala Ile Gln Glu Leu Phe Lys Arg Ile Ser Glu Gln
            370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
            435                 440

<210> SEQ ID NO 15
<211> LENGTH: 444
<212> TYPE: PRT
<213> ORGANISM: Cricetulus griseus
<220> FEATURE:
<221> NAME/KEY: VARIANT
<222> LOCATION: (215)..(215)
<223> OTHER INFORMATION: Leu to Pro beta-tubulin substitutional variant.

<400> SEQUENCE: 15

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
        50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
            85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
            115                 120                 125

Cys Leu Gln Gly Phe Gln Leu Thr His Ser Leu Gly Gly Gly Thr Gly
        130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Pro Lys Leu Thr Thr Pro Thr Tyr Gly Asp
    210                 215                 220

Leu Asn His Leu Val Ser Ala Thr Met Ser Gly Val Thr Thr Cys Leu
```

-continued

```
                225                 230                 235                 240
Arg Phe Pro Gly Gln Leu Asn Ala Asp Leu Arg Lys Leu Ala Val Asn
                245                 250                 255
Met Val Pro Phe Pro Arg Leu His Phe Phe Met Pro Gly Phe Ala Pro
            260                 265                 270
Leu Thr Ser Arg Gly Ser Gln Gln Tyr Arg Ala Leu Thr Val Pro Glu
        275                 280                 285
Leu Thr Gln Gln Val Phe Asp Ala Lys Asn Met Met Ala Ala Cys Asp
    290                 295                 300
Pro Arg His Gly Arg Tyr Leu Thr Val Ala Ala Val Phe Arg Gly Arg
305                 310                 315                 320
Met Ser Met Lys Glu Val Asp Glu Gln Met Leu Asn Val Gln Asn Lys
                325                 330                 335
Asn Ser Ser Tyr Phe Val Glu Trp Ile Pro Asn Asn Val Lys Thr Ala
            340                 345                 350
Val Cys Asp Ile Pro Pro Arg Gly Leu Lys Met Ala Val Thr Phe Ile
        355                 360                 365
Gly Asn Ser Thr Ala Ile Gln Glu Leu Phe Lys Arg Ile Ser Glu Gln
    370                 375                 380
Phe Thr Ala Met Phe Arg Arg Lys Ala Phe Leu His Trp Tyr Thr Gly
385                 390                 395                 400
Glu Gly Met Asp Glu Met Glu Phe Thr Glu Ala Ser Asn Met Asn
                405                 410                 415
Asp Leu Val Ser Glu Tyr Gln Gln Tyr Gln Asp Ala Thr Ala Glu Glu
            420                 425                 430
Glu Glu Asp Phe Gly Glu Glu Ala Glu Glu Ala
        435                 440

<210> SEQ ID NO 16
<211> LENGTH: 444
<212> TYPE: PRT
<213> ORGANISM: Cricetulus griseus
<220> FEATURE:
<221> NAME/KEY: VARIANT
<222> LOCATION: (215)..(215)
<223> OTHER INFORMATION: Leu to Met beta-tubulin substitutional variant.

<400> SEQUENCE: 16

Met Arg Glu Ile Val His Ile Gln Ala Gly Gln Cys Gly Asn Gln Ile
1               5                   10                  15
Gly Ala Lys Phe Trp Glu Val Ile Ser Asp Glu His Gly Ile Asp Pro
            20                  25                  30
Thr Gly Thr Tyr His Gly Asp Ser Asp Leu Gln Leu Asp Arg Ile Ser
        35                  40                  45
Val Tyr Tyr Asn Glu Ala Thr Gly Gly Lys Tyr Val Pro Arg Ala Ile
    50                  55                  60
Leu Val Asp Leu Glu Pro Gly Thr Met Asp Ser Val Arg Ser Gly Pro
65                  70                  75                  80
Phe Gly Gln Ile Phe Arg Pro Asp Asn Phe Val Phe Gly Gln Ser Gly
                85                  90                  95
Ala Gly Asn Asn Trp Ala Lys Gly His Tyr Thr Glu Gly Ala Glu Leu
            100                 105                 110
Val Asp Ser Val Leu Asp Val Val Arg Lys Glu Ala Glu Ser Cys Asp
        115                 120                 125
Cys Leu Gln Gly Phe Gln Leu Thr His Ser Leu Gly Gly Gly Thr Gly
    130                 135                 140
```

```
Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Met Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
                260                 265                 270

Leu Thr Ser Arg Gly Ser Gln Gln Tyr Arg Ala Leu Thr Val Pro Glu
                275                 280                 285

Leu Thr Gln Gln Val Phe Asp Ala Lys Asn Met Met Ala Ala Cys Asp
290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
                340                 345                 350

Val Cys Asp Ile Pro Pro Arg Gly Leu Lys Met Ala Val Thr Phe Ile
                355                 360                 365

Gly Asn Ser Thr Ala Ile Gln Glu Leu Phe Lys Arg Ile Ser Glu Gln
                370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
                420                 425                 430

Glu Glu Asp Phe Gly Glu Glu Ala Glu Glu Ala
                435                 440

<210> SEQ ID NO 17
<211> LENGTH: 444
<212> TYPE: PRT
<213> ORGANISM: Cricetulus griseus
<220> FEATURE:
<221> NAME/KEY: VARIANT
<222> LOCATION: (215)..(215)
<223> OTHER INFORMATION: Leu to Glu beta-tubulin substitutional variant.

<400> SEQUENCE: 17

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Thr Tyr His Gly Asp Ser Asp Leu Gln Leu Asp Arg Ile Ser
            35                  40                  45
```

```
Val Tyr Tyr Asn Glu Ala Thr Gly Gly Lys Tyr Val Pro Arg Ala Ile
 50                  55                  60
Leu Val Asp Leu Glu Pro Gly Thr Met Asp Ser Val Arg Ser Gly Pro
 65                  70                  75                  80
Phe Gly Gln Ile Phe Arg Pro Asp Asn Phe Val Phe Gly Gln Ser Gly
                 85                  90                  95
Ala Gly Asn Asn Trp Ala Lys Gly His Tyr Thr Glu Gly Ala Glu Leu
            100                 105                 110
Val Asp Ser Val Leu Asp Val Val Arg Lys Glu Ala Glu Ser Cys Asp
            115                 120                 125
Cys Leu Gln Gly Phe Gln Leu Thr His Ser Leu Gly Gly Gly Thr Gly
130                 135                 140
Ser Gly Met Gly Thr Leu Leu Ile Ser Lys Ile Arg Glu Glu Tyr Pro
145                 150                 155                 160
Asp Arg Ile Met Asn Thr Phe Ser Val Val Pro Ser Pro Lys Val Ser
                165                 170                 175
Asp Thr Val Val Glu Pro Tyr Asn Ala Thr Leu Ser Val His Gln Leu
            180                 185                 190
Val Glu Asn Thr Asp Glu Thr Tyr Cys Ile Asp Asn Glu Ala Leu Tyr
            195                 200                 205
Asp Ile Cys Phe Arg Thr Glu Lys Leu Thr Thr Pro Thr Tyr Gly Asp
210                 215                 220
Leu Asn His Leu Val Ser Ala Thr Met Ser Gly Val Thr Thr Cys Leu
225                 230                 235                 240
Arg Phe Pro Gly Gln Leu Asn Ala Asp Leu Arg Lys Leu Ala Val Asn
                245                 250                 255
Met Val Pro Phe Pro Arg Leu His Phe Phe Met Pro Gly Phe Ala Pro
            260                 265                 270
Leu Thr Ser Arg Gly Ser Gln Gln Tyr Arg Ala Leu Thr Val Pro Glu
            275                 280                 285
Leu Thr Gln Gln Val Phe Asp Ala Lys Asn Met Met Ala Ala Cys Asp
290                 295                 300
Pro Arg His Gly Arg Tyr Leu Thr Val Ala Ala Val Phe Arg Gly Arg
305                 310                 315                 320
Met Ser Met Lys Glu Val Asp Glu Gln Met Leu Asn Val Gln Asn Lys
                325                 330                 335
Asn Ser Ser Tyr Phe Val Glu Trp Ile Pro Asn Asn Val Lys Thr Ala
            340                 345                 350
Val Cys Asp Ile Pro Pro Arg Gly Leu Lys Met Ala Val Thr Phe Ile
            355                 360                 365
Gly Asn Ser Thr Ala Ile Gln Glu Leu Phe Lys Arg Ile Ser Glu Gln
370                 375                 380
Phe Thr Ala Met Phe Arg Arg Lys Ala Phe Leu His Trp Tyr Thr Gly
385                 390                 395                 400
Glu Gly Met Asp Glu Met Glu Phe Thr Glu Ala Glu Ser Asn Met Asn
                405                 410                 415
Asp Leu Val Ser Glu Tyr Gln Gln Tyr Gln Asp Ala Thr Ala Glu Glu
            420                 425                 430
Glu Glu Asp Phe Gly Glu Glu Ala Glu Glu Ala
            435                 440

<210> SEQ ID NO 18
<211> LENGTH: 444
<212> TYPE: PRT
```

```
<213> ORGANISM: Cricetulus griseus
<220> FEATURE:
<221> NAME/KEY: VARIANT
<222> LOCATION: (215)..(215)
<223> OTHER INFORMATION: Leu to Phe beta-tubulin substitutional variant.

<400> SEQUENCE: 18
```

| | | | | | | | | | | | | | | |
|---|---|---|---|---|---|---|---|---|---|---|---|---|---|---|
| Met | Arg | Glu | Ile | Val | His | Ile | Gln | Ala | Gly | Gln | Cys | Gly | Asn | Gln | Ile |
| 1 | | | | 5 | | | | | 10 | | | | | 15 | |

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
        50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Phe Lys Leu Thr Thr Pro Thr Tyr Gly Asp
210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
370                 375                 380

```
Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
            405                 410                 415

Asp Leu Val Ser Glu Tyr Gln Tyr Gln Asp Ala Thr Ala Glu Glu
            420                 425                 430

Glu Glu Asp Phe Gly Glu Glu Ala Glu Glu Ala
            435                 440
```

<210> SEQ ID NO 19
<211> LENGTH: 444
<212> TYPE: PRT
<213> ORGANISM: Cricetulus griseus
<220> FEATURE:
<221> NAME/KEY: VARIANT
<222> LOCATION: (215)..(215)
<223> OTHER INFORMATION: Leu to His beta-tubulin substitutional variant.

<400> SEQUENCE: 19

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
        50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr His Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285
```

```
Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
        435                 440

<210> SEQ ID NO 20
<211> LENGTH: 444
<212> TYPE: PRT
<213> ORGANISM: Cricetulus griseus

<400> SEQUENCE: 20

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Arg Lys Leu Thr Thr Pro Thr Tyr Gly Asp
    210                 215                 220
```

-continued

```
Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
                340                 345                 350

Val Cys Asp Ile Pro Pro Arg Gly Leu Lys Met Ala Val Thr Phe Ile
            355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
                420                 425                 430

Glu Glu Asp Phe Gly Glu Glu Ala Glu Glu Ala
                435                 440

<210> SEQ ID NO 21
<211> LENGTH: 444
<212> TYPE: PRT
<213> ORGANISM: Cricetulus griseus
<220> FEATURE:
<221> NAME/KEY: VARIANT
<222> LOCATION: (216)..(216)
<223> OTHER INFORMATION: Lys to Ala beta-tubulin substitutional variant.

<400> SEQUENCE: 21

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125
```

```
Cys Leu Gln Gly Phe Gln Leu Thr His Ser Leu Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Ala Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Glu Ala
        435                 440

<210> SEQ ID NO 22
<211> LENGTH: 444
<212> TYPE: PRT
<213> ORGANISM: Cricetulus griseus
<220> FEATURE:
<221> NAME/KEY: VARIANT
<222> LOCATION: (217)..(217)
<223> OTHER INFORMATION: Leu to Ala beta-tubulin substitutional variant.

<400> SEQUENCE: 22

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
```

```
            35                  40                  45
Val Tyr Tyr Asn Glu Ala Thr Gly Gly Lys Tyr Val Pro Arg Ala Ile
 50                  55                  60

Leu Val Asp Leu Glu Pro Gly Thr Met Asp Ser Val Arg Ser Gly Pro
 65                  70                  75                  80

Phe Gly Gln Ile Phe Arg Pro Asp Asn Phe Val Phe Gly Gln Ser Gly
                 85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Ala Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
        435                 440

<210> SEQ ID NO 23
```

```
<211> LENGTH: 444
<212> TYPE: PRT
<213> ORGANISM: Cricetulus griseus
<220> FEATURE:
<221> NAME/KEY: VARIANT
<222> LOCATION: (217)..(217)
<223> OTHER INFORMATION: Leu to Arg beta-tubulin substitutional variant.

<400> SEQUENCE: 23
```

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Arg Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365
```

```
Gly Asn Ser Thr Ala Ile Gln Glu Leu Phe Lys Arg Ile Ser Glu Gln
        370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Glu Ala
        435                 440

<210> SEQ ID NO 24
<211> LENGTH: 444
<212> TYPE: PRT
<213> ORGANISM: Cricetulus griseus
<220> FEATURE:
<221> NAME/KEY: VARIANT
<222> LOCATION: (228)..(228)
<223> OTHER INFORMATION: Leu to Ala beta-tubulin substitutional variant.

<400> SEQUENCE: 24

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Ala Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
```

-continued

```
            275                 280                 285
Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
                340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
                420                 425                 430

Glu Glu Asp Phe Gly Glu Glu Ala Glu Glu Ala
        435                 440
```

<210> SEQ ID NO 25
<211> LENGTH: 444
<212> TYPE: PRT
<213> ORGANISM: Cricetulus griseus
<220> FEATURE:
<221> NAME/KEY: VARIANT
<222> LOCATION: (228)..(228)
<223> OTHER INFORMATION: Leu to Phe beta-tubulin substitutional variant.

<400> SEQUENCE: 25

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190
```

-continued

```
Val Glu Asn Thr Asp Glu Thr Tyr Cys Ile Asp Asn Glu Ala Leu Tyr
            195                 200                 205

Asp Ile Cys Phe Arg Thr Leu Lys Leu Thr Thr Pro Thr Tyr Gly Asp
            210                 215                 220

Leu Asn His Phe Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
            245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
            275                 280                 285

Leu Thr Gln Gln Val Phe Asp Ala Lys Asn Met Met Ala Ala Cys Asp
            290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
            325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
            355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
            405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
            435                 440
```

<210> SEQ ID NO 26
<211> LENGTH: 444
<212> TYPE: PRT
<213> ORGANISM: Cricetulus griseus
<220> FEATURE:
<221> NAME/KEY: VARIANT
<222> LOCATION: (228)..(228)
<223> OTHER INFORMATION: Leu to His beta-tubulin substitutional variant.
<300> PUBLICATION INFORMATION:
<301> AUTHORS: M. L. Gonzalez-Garay, L. Chang, K. Blade, D. R. Menick
    and F. Cabral
<302> TITLE: A B-Tubulin Leucine Cluster Involved in Microtubule
    Assembly and
<303> JOURNAL: Journal of Biological Chemistry
<304> VOLUME: 274
<305> ISSUE: 34
<306> PAGES: 23875-23882
<307> DATE: 1999-08-20
<313> RELEVANT RESIDUES: (2)..(7)

<400> SEQUENCE: 26

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
```

-continued

```
                35                  40                  45
Val Tyr Tyr Asn Glu Ala Thr Gly Gly Lys Tyr Val Pro Arg Ala Ile
 50                  55                  60
Leu Val Asp Leu Glu Pro Gly Thr Met Asp Ser Val Arg Ser Gly Pro
 65                  70                  75                  80
Phe Gly Gln Ile Phe Arg Pro Asp Asn Phe Val Phe Gly Gln Ser Gly
                 85                  90                  95
Ala Gly Asn Asn Trp Ala Lys Gly His Tyr Thr Glu Gly Ala Glu Leu
                100                 105                 110
Val Asp Ser Val Leu Asp Val Val Arg Lys Glu Ala Glu Ser Cys Asp
                115                 120                 125
Cys Leu Gln Gly Phe Gln Leu Thr His Ser Leu Gly Gly Gly Thr Gly
                130                 135                 140
Ser Gly Met Gly Thr Leu Leu Ile Ser Lys Ile Arg Glu Glu Tyr Pro
145                 150                 155                 160
Asp Arg Ile Met Asn Thr Phe Ser Val Val Pro Ser Pro Lys Val Ser
                165                 170                 175
Asp Thr Val Val Glu Pro Tyr Asn Ala Thr Leu Ser Val His Gln Leu
                180                 185                 190
Val Glu Asn Thr Asp Glu Thr Tyr Cys Ile Asp Asn Glu Ala Leu Tyr
                195                 200                 205
Asp Ile Cys Phe Arg Thr Leu Lys Leu Thr Thr Pro Thr Tyr Gly Asp
                210                 215                 220
Leu Asn His His Val Ser Ala Thr Met Ser Gly Val Thr Thr Cys Leu
225                 230                 235                 240
Arg Phe Pro Gly Gln Leu Asn Ala Asp Leu Arg Lys Leu Ala Val Asn
                245                 250                 255
Met Val Pro Phe Pro Arg Leu His Phe Phe Met Pro Gly Phe Ala Pro
                260                 265                 270
Leu Thr Ser Arg Gly Ser Gln Tyr Arg Ala Leu Thr Val Pro Glu
                275                 280                 285
Leu Thr Gln Gln Val Phe Asp Ala Lys Asn Met Met Ala Ala Cys Asp
290                 295                 300
Pro Arg His Gly Arg Tyr Leu Thr Val Ala Ala Val Phe Arg Gly Arg
305                 310                 315                 320
Met Ser Met Lys Glu Val Asp Glu Gln Met Leu Asn Val Gln Asn Lys
                325                 330                 335
Asn Ser Ser Tyr Phe Val Glu Trp Ile Pro Asn Asn Val Lys Thr Ala
                340                 345                 350
Val Cys Asp Ile Pro Pro Arg Gly Leu Lys Met Ala Val Thr Phe Ile
                355                 360                 365
Gly Asn Ser Thr Ala Ile Gln Glu Leu Phe Lys Arg Ile Ser Glu Gln
                370                 375                 380
Phe Thr Ala Met Phe Arg Arg Lys Ala Phe Leu His Trp Tyr Thr Gly
385                 390                 395                 400
Glu Gly Met Asp Glu Met Glu Phe Thr Glu Ala Glu Ser Asn Met Asn
                405                 410                 415
Asp Leu Val Ser Glu Tyr Gln Gln Tyr Gln Asp Ala Thr Ala Glu Glu
                420                 425                 430
Glu Glu Asp Phe Gly Glu Glu Ala Glu Glu Ala
                435                 440
```

I claim:

1. A method for determining the insensitivity of a patient sample to paclitaxel-like drugs, comprising:
   (a) obtaining a patient sample;
   (b) determining if said patient's beta-tubulin comprises an amino acid substitution at one or more of positions 214, 215, 216, 217 or 228 relative to the wildtype sequence; and
   (c) correlating the presence of said mutation with patient insensitivity to paclitaxel-like drugs.

2. A method for determining the insensitivity of a patient sample to drugs which stabilize microtubule assembly, comprising:
   (a) hybridizing an oligonucleotide to nucleic acid from the patient sample, wherein said oligonucleotide is complementary to a wild-type encoding sequence of an H6H7 region of the patient's beta-tubulin or an encoding sequence having at least one mutation of an H6H7 region of the patient's beta-tubulin; and
   (b) detecting hybridization between the oligonucleotide and the nucleic acid, the identity of the nucleotide indicating whether the sample is insensitive to drugs which stabilize microtubule assembly.

3. The method of claim 2, wherein the oligonucleotide is immobilized to a solid support.

4. The method of claim 2, wherein the sample nucleic acid is labeled and the oligonucleotide is unlabeled.

5. A method of screening a patient being or to be treated with a paclitaxel-like drug comprising:
   (a) obtaining a sample from the patient;
   (b) detecting one or more substitutions in an H6H7 region of a beta-tubulin polypeptide from the patient sample; and
   (c) correlating said one or more substitutions with decreased sensitivity to the paclitaxel-like drug.

6. The method of claim 5 wherein said substitution is a leucine substitution at amino acid position 214, 215, 216, 21 and 228, or any combination thereof.

7. A method of determining paclitaxel insensitivity in a sample from a cancer patient comprising the steps of:
   (a) detecting a mutation in a nucleic acid encoding tubulin protein in the sample, the mutation comprising one or more mutations within the nucleic acid encoding amino acids 214, 215, 216, 217, and 228; and
   (b) correlating detection of the mutation with paclitaxel insensitivity.

8. The method of claim 1, wherein said substitution is at position 214.

9. The method of claim 1, wherein said substitution is at position 215.

10. The method of claim 1, wherein said substitution is at position 216.

11. The method of claim 1, wherein said substitution is at position 217.

12. The method of claim 1, wherein said substitution is at position 228.

13. The method of claim wherein 2, said mutation occurs at amino acid positions 214, 215, 216, 217, and 228, or any combination thereof.

14. The method of claim 2, wherein said mutation is at position 214.

15. The method of claim 2, wherein said mutation is at position 215.

16. The method of claim 2, wherein said mutation is at position 216.

17. The method of claim 2, wherein said mutation is at position 217.

18. The method of claim 2, wherein said mutation is at position 228.

19. The method of claim 6, wherein said substitution is at position 214.

20. The method of claim 6, wherein said substitution is at position 215.

21. The method of claim 6, wherein said substitution is at position 216.

22. The method of claim 6, wherein said substitution is at position 217.

23. The method of claim 6, wherein said substitution is at position 228.

24. The method of claim 7, wherein said mutation is at position 214.

25. The method of claim 7, wherein said mutation is at position 215.

26. The method of claim 7, wherein said mutation is at position 216.

27. The method of claim 7, wherein said mutation is at position 217.

28. The method of claim 7, wherein said mutation is at position 228.

* * * * *

UNITED STATES PATENT AND TRADEMARK OFFICE
CERTIFICATE OF CORRECTION

| | | |
|---|---|---|
| PATENT NO. | : 7,179,588 B1 | Page 1 of 1 |
| APPLICATION NO. | : 09/574099 | |
| DATED | : February 20, 2007 | |
| INVENTOR(S) | : Fernando Cabral | |

It is certified that error appears in the above-identified patent and that said Letters Patent is hereby corrected as shown below:

Claim 6
In column 85, line 37, delete "21" and insert -- 217, -- .

Claim 13
In column 86, line 11, delete "wherein 2," and insert -- 2, wherein -- .

Signed and Sealed this

Tenth Day of April, 2007

JON W. DUDAS
*Director of the United States Patent and Trademark Office*